US009339239B2

(12) United States Patent
Wang et al.

(10) Patent No.: US 9,339,239 B2
(45) Date of Patent: May 17, 2016

(54) METHODS AND DEVICES FOR OPTIMIZATION OF MAGNETIC RESONANCE IMAGING PROTOCOLS

(71) Applicant: Ohio State Innovation Foundation, Columbus, OH (US)

(72) Inventors: Jinghua Wang, Columbus, OH (US); Zhong-lin Lu, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 213 days.

(21) Appl. No.: 14/023,388

(22) Filed: Sep. 10, 2013

(65) Prior Publication Data

US 2015/0071514 A1     Mar. 12, 2015

(51) Int. Cl.
| | |
|---|---|
| *G06K 9/00* | (2006.01) |
| *A61B 5/00* | (2006.01) |
| *G01R 33/54* | (2006.01) |
| *A61B 5/055* | (2006.01) |
| *G01R 33/48* | (2006.01) |
| *G01R 33/58* | (2006.01) |

(52) U.S. Cl.
CPC ............ *A61B 5/7221* (2013.01); *G01R 33/543* (2013.01); *A61B 5/055* (2013.01); *G01R 33/482* (2013.01); *G01R 33/4824* (2013.01); *G01R 33/586* (2013.01)

(58) Field of Classification Search
CPC .................. G06T 7/0012; G06T 2207/10088; G06T 2207/30004
See application file for complete search history.

(56) References Cited

U.S. PATENT DOCUMENTS

| | | | |
|---|---|---|---|
| 4,707,658 | A | 11/1987 | Frahm et al. |
| 5,245,282 | A | 9/1993 | Mugler, III et al. |
| 5,551,431 | A | 9/1996 | Wells, III et al. |
| 6,400,151 | B1 | 6/2002 | Haase et al. |

(Continued)

OTHER PUBLICATIONS

Bampton, A.E., et al., "Centric Phase-Encoding Order in Three-dimensional MP-RAGE Sequences: Application to Abdominal Imaging," Journal of Magnetic Resonance Imaging, vol. 2, No. 3, 1992, pp. 327-334.

(Continued)

*Primary Examiner* — Vu Le
*Assistant Examiner* — Guillermo Rivera-Martinez
(74) *Attorney, Agent, or Firm* — Meunier Carlin & Curfman LLC

(57) ABSTRACT

MRI techniques are widely and successfully applied in medicine and biophysics because MRI provides good contrast between different soft tissues without ionizing radiation. MRI protocols are optimized in four aspects: imaging parameters, k-space strategies, RF system calibration and contrast inhomogeneity correction. The signal intensities of normal and disease tissues are simulated, for example, using Bloch equations for an imaging sequence with tissue MR parameters. The relationships between imaging parameters and tissue contrasts are calculated using the numerically simulated signal intensities. The optimal imaging parameters and/or k-space strategies are determined to maximize image contrast and minimize artifacts with acceptable spatial-temporal resolution based on characterization of the imaging hardware. The RF system is optionally calibrated to improve the accuracy of the imaging parameters and reduce inter-scanner variability. Additionally, contrast-to-noise inhomogeneity caused by transmit field and receive sensitivity is optionally corrected by optimal flip angle and measured receiver sensitivity.

8 Claims, 21 Drawing Sheets

(56) References Cited

U.S. PATENT DOCUMENTS

| | | |
|---|---|---|
| 7,078,899 B2 | 7/2006 | Dale et al. |
| 7,489,962 B2 | 2/2009 | Cull et al. |
| 7,515,951 B2 | 4/2009 | Egan et al. |
| 7,705,597 B2 | 4/2010 | Horger et al. |
| 7,715,899 B2 | 5/2010 | Harvey et al. |
| 7,821,266 B2 | 10/2010 | Feiweier |
| 8,319,495 B1* | 11/2012 | Zhu ................................ 324/307 |
| 2003/0030435 A1* | 2/2003 | Venkatesan et al. .......... 324/306 |
| 2008/0129298 A1* | 6/2008 | Vaughan et al. ............. 324/322 |
| 2008/0150532 A1* | 6/2008 | Slavin et al. ................. 324/318 |
| 2010/0004909 A1 | 1/2010 | Nitz |
| 2010/0127703 A1* | 5/2010 | Sung et al. .................... 324/309 |
| 2010/0239151 A1* | 9/2010 | Dannels et al. ............... 382/131 |
| 2012/0032676 A1 | 2/2012 | Dannels |
| 2013/0038326 A1* | 2/2013 | Amadon et al. .............. 324/309 |
| 2014/0039300 A1* | 2/2014 | Gjesdal et al. ................ 600/420 |

OTHER PUBLICATIONS

Tardif, C.L., et al., "Regional Impact of Field Strength on Voxel-Based Morphometry Results," Human Brain Mapping, vol. 31, 2010, pp. 943-957.

Wang, J., et al., "In Vivo Method for Correcting Transmit/Receive Nonuniformities with Phased Array Coils," Magnetic Resonance in Medicine, vol. 53, 2005, pp. 666-674.

Wang, J., et al., "Measurement and Correction of Transmitter and Receiver Induced Nonuniformities in Vivo," Magnetic Resonance in Medicine, vol. 53, 2005, pp. 408-417.

* cited by examiner

Figure 10 (comparison)

METHODS AND DEVICES FOR OPTIMIZATION OF MAGNETIC RESONANCE IMAGING PROTOCOLS

BACKGROUND

Magnetic Resonance Imaging (MRI) is one of the most important modern medical imaging modalities. It has far less risk of side effects than most other imaging modalities such as radioscopy with x-rays or computed tomography because patient and medical personal are not subjected to ionizing radiation exposure in the procedure. The use of MRI has grown very fast. Every year, more than 30 million MRI scans are performed in the United States; more than 60 million MRI scans are performed worldwide. Doctors often recommend MRI for the diagnoses of various diseases, such as tumors, strokes, heart problems, and spine disease. A high-quality scan is important for maximizing diagnostic sensitivity and making the right diagnosis. Generally, a high quality image requires high signal to noise ratio (SNR), high contrast between normal and pathological tissues, low levels of artifact, and reasonable and acceptable spatial-temporal resolution.

In order to obtain a detectable MR signal, the object examined is positioned in a homogeneous static magnetic field so that the object's nuclear spins generate net magnetization oriented along the static magnetic field. The net magnetization is rotated away from the static magnetic field using a radio frequency (RF) excitation field with the same frequency as the Larmor frequency of the nucleus. The rotated angle is determined by the field strength of the RF excitation pulse and its duration. In the end of the RF excitation pulse, the nuclei, in relaxing to their normal spin conditions, generate a decaying signal (the "MR signal") at the same radio frequency as that used for excitation. The MR signal is picked up by a receive coil, amplified and processed. The acquired measurements are digitized and stored as complex numerical values in a "k-space" matrix. An associated MR image can be reconstructed from the k-space data, for example, by an inverse 2D or 3D fast Fourier transform (FFT) from raw data, which are collected in the spatial frequency domain (the "k-space").

SUMMARY

Described herein are methods and devices for optimization of MRI protocols (including the optimization of imaging parameters, k-space strategies and RF system calibration) to enhance image quality and improve detection sensitivity of path-physiological changes. Additionally, methods and devices to correct inhomogeneous contrast caused by non-uniform transmit field and receiver sensitivity are described.

Disclosed herein are optimized MRI protocols for acquiring high quality MRI images. In accordance with this disclosure there is provided a method which simulates signal intensity and contrast using Bloch equations with tissue MR parameters. Other implementations of this disclosure provide initial imaging parameters for further optimization of imaging parameters. The initial optimal imaging parameters are determined by the relationship between imaging parameters and tissue contrasts. Yet other implementations provide a method for optimizing k-space strategies. K-space center is filled with the k-space line that gives rise to the maximum contrast. Optimized k-space strategy is determined by both maximal contrast and minimal image artifacts. The disclosure further provides a method for optimizing k-space strategies for limited k-space strategies. This disclosure also describes the use of RF calibration to reduce variability caused by hardware systems. Another implementation of the disclosure is to reduce or eliminate the contrast inhomogeneity caused by both transmit field and receive sensitivity. Also provided is a technique for evaluating performance of the imaging parameters in MRI.

In accordance with other aspects of the disclosure are systems and methods to optimize imaging parameters and/or k-space strategies so that high quality MR images can be acquired using current MRI facility. This is achieved by a method for simulation and iterative actual measurements including the following steps: obtaining one or more MR parameters for a tissue, where the tissue includes a normal or pathological (e.g., diseased) tissue, simulating at least one image quality metric (e.g., using Bloch equations) for the MRI sequence and the MR parameters for the tissue, where the image quality metric includes a contrast metric, optimizing one or more imaging parameters by maximizing the image quality metric and minimizing an image artifact, and acquiring the MR images using the optimized imaging parameters.

Optionally, the MRI sequence can be any MRI sequence for acquiring MR images of a subject with acceptable spatial-temporal resolution. For example, the MRI sequence can be any one of gradient echo sequence (including the MP-RAGE or FLASH sequence, for example), echo planar sequence, spin echo sequence and rapid acquisition relation enhanced imaging (e.g., turbo spin echo, fast spin echo). The MRI sequence can also be combined with one or more of parallel imaging techniques, compress sensing and/or contrast agent MRI. It should be understood, however, that the above MRI sequences are provided only as examples and that this disclosure contemplates using other MRI sequences.

Optionally, the one or more imaging parameters include, but are not limited to, a repetition time (TR), an echo time (TE), a variable flip angle, a variable refocusing angle, magnetization preparation pulses, fat saturation pulses, inversion times, a bandwidth, an echo train length, an echo space time or a readout RF number. Alternatively or additionally, the one or more imaging parameters are within predetermined ranges imposed by hardware system or safety limitations. For example, the hardware system (e.g., one or more magnets and gradient strength thereof, RF coil, acquisition bandwidth, etc.) can limit the range of useable imaging parameters. Similarly, safety limitations such as specific absorption rate or nerve stimulation can also limit the range of useable imaging parameters. This disclosure contemplates that the optimized imaging parameters can be selected from within the predetermined ranges. Optionally, the one or more imaging parameters facilitate detection of at least one of a path-physiological change, physiological change, electrophysiological change or disease in tissue.

Optionally, the image quality metric includes, but is not limited to, signal intensity, SNR, SNR efficiency, contrast, contrast-to-noise (CNR) or CNR efficiency. Additionally, the image artifact includes, but is not limited to, signal inhomogeneity, SNR inhomogeneity, contrast inhomogeneity, CNR inhomogeneity, signal loss, geometry distortion or image ghost.

Optionally, the MR parameters are static field strength and pathophysiology dependent. Optionally, the MR parameters can be normal or abnormal MR parameters. For example, the MR parameters include, but are not limited to, $T_1$ relaxation, $T_2$ relaxation, $T_2$ star relaxation, proton density, diffusion, magnetic susceptibility, oxygen/deoxgen-hemoglobin or magnetization transfer. This disclosure contemplates that the MR parameters can include other parameters related to signal intensity and tissue contrast. It should be understood that the MR parameters can be obtained from literature and/or by experiment.

Optionally, as described above, the method can further include performing a calibration to determine a calibration factor, where the calibration factor relates theoretical imaging parameters to actual imaging parameters of an MRI scanner, correcting the optimized imaging parameters based on the calibration factor, and acquiring the MR images with the MRI scanner using the corrected imaging parameters.

Alternatively or additionally, the method can further include refining the optimized imaging parameters based on the acquired MR images.

Optionally, the MRI images are acquired using an optimal k-space strategy or a predetermined k-space strategy.

Most MR image information (contrast and general shape) is contained in the center of the k-space. The low-spatial-frequency components in the center of the k-space have the highest amplitudes, giving rise to the greatest changes in image contrast. High-spatial-frequency components in the peripheral of the k-space have lower amplitudes. They have very little effect on image contrast or general shape but sharpen the image as they encode edges. The higher the spatial frequency the k-space covers, the better the spatial resolution will be. Therefore, the k-space zero line largely determines image contrast. With a rectilinear k-space trajectory, there are three k-space sampling orders: sequential order, centric order, and reverse centric order. These conventional k-space sampling orders limit k-space zero filling into specific position (beginning, center, and end), and restrict the optimization of k-space strategies. The optimization of k-space strategy is achieved with the following steps: setting independent image parameters, where the independent image parameters are independent of a k-space strategy in an imaging sequence, simulating a relationship between each respective k-space acquisition and at least one image quality metric that includes a contrast metric, optimizing the k-space strategy to maximize the image quality metric and minimize an image artifact, and acquiring at least one MR image using the optimized k-space strategy. The independent image parameters are set according to one of MRI safety (such as specific absorption rate), hardware limitation (such as gradient strength), and expected image resolution.

Optionally, the independent image parameters can include repetition time (TR), spatial resolution, repetition time, acquisition bandwidth, and parallel acquisition factors in MRI sequences.

Optionally, the k-space strategy includes a k-space trajectory and a sampling order. An example sampling order is an order consistent with contrast order from maximum to minimum contrast metric, for example. The k-space trajectory can include at least one of rectilinear, radial, echo planar imaging, spiral, projection reconstruction, random k-space trajectory, under-sampled k-space trajectory, and partial k-space sampling trajectory and the sampling order can include at least one of a sequential, centric, interleave, reverse or random sampling order. Optionally, the optimal k-space strategy is the k-space trajectory and sampling order that achieves maximum contrast and minimum image artifact, for example, as determined by computer simulation. In some instances, a trade-off between contrast and image artifact is considered, particularly if k-space zero line filling leads to a large image artifact.

Alternatively or additionally, optimizing the k-space strategy to maximize the image quality metric and minimize an image artifact optionally further includes filling a k-space zero line using a k-space acquisition having the maximum contrast metric, where the contrast metric includes at least one of a contrast, CNR or a CNR efficiency, and designing a k-space trajectory and/or sampling order to minimize the image artifact, where the image artifact comprises at least one of signal inhomogeneity, SNR inhomogeneity, contrast inhomogeneity, CNR inhomogeneity, signal loss, geometry distortion or image ghost. Optionally, the optimal k-space zero line corresponds to a maximum contrast, CNR or CNR efficiency. The contrast of each k-space center can optionally depend on echo space time, inversion recovery time, flip angle or the number of RF readout pulses, for example.

Alternatively or additionally, simulating a relationship between each respective k-space acquisition and at least one image quality metric optionally further includes using Bloch equations for the imaging sequence and tissue MR parameters (described above). One or more imaging parameters that are both dependent and independent on the k-space strategy can also be used in the Bloch equations.

Optionally, the imaging sequence includes at least one of a gradient echo sequence, an echo planar sequence or a spin echo sequence with or without magnetization preparation.

Optionally, the image quality metric includes at least one of signal intensity, SNR, SNR efficiency, contrast, CNR and CNR efficiency.

Optionally, optimizing the k-space strategy to maximize the image quality metric and minimize the image artifact further includes optimizing the k-space strategy under limited conditions, where the limited conditions include at least one of a predetermined k-space trajectory, a predetermined sampling order or predetermined imaging parameters. It should be understood that an MRI scanner may have limited conditions, for example, as imposed by hardware system or safety limitations as described above. Thus, this disclosure contemplates that the k-space strategy can be optimized within the limited conditions.

Generally, RF system calibration is based on virtual objects. The flip angle in MRI protocols is estimated based on the calibration. In practice, the coupling between coil configuration and a physical object strongly affect RF distribution and RF calibration factor. The position and orientation between the physical object and the coil will also lead to changes in calibration. Thus, it is necessary to calibrate the RF system in vivo. A RF system can be calibrated by putting an object in an MR scanner for in vivo RF system calibration, acquiring a set of signal intensity images of the object by using MR scans conducted at different flip angles in vivo, estimating a relative flip angle map and then relative transmit field maps with the images acquired at different flip angles, determining the calibration factor of the transmit RF field or flip angles with the assumption of a linear relationship between nominal flip angles and the measured flip angles and correcting absolute flip angles using the calibration factor.

Optionally, the estimated transmit field is determined by estimating a relative flip angle map using the image SI(x), estimating a relative transmit field map for the plurality of signal intensity images, each acquired using different imaging parameters, determining a calibration factor based on a linear relationship between the nominal flip angles and the measured flip angles for each nominal flip angle, and calculating an absolute flip angle corresponding to the nominal flip angles for each nominal flip angle.

Optionally, the calibration factor of RF field or flip angle is calculated with the measured flip angles or the signal intensity of the images with various flip angles. The method to determine the actual flip angles is based on a linear relationship between the measured flip angles and nominal flip angles.

Image inhomogeneity caused by RF coil configuration and wave behavior can lead to position dependent signal intensity and contrast. The effect of CNR inhomogeneity on image quality becomes important at tissue boundaries when partial volume effect is considered. CNR inhomogeneity caused by transmit field can be corrected by simulating tissue contrast for an MRI acquisition sequence (e.g., using Bloch equations), finding one or more optimal imaging parameters for reducing a sensitivity of a contrast inhomogeneity caused by non-uniform acquisition conditions such as non-uniform transmit field, for example. The method can also include acquiring a set of signal intensity images using the optimal imaging parameters, estimating a receive sensitivity, registering the receive sensitivity with the set of signal intensity images to produce a relative correction matrix, normalizing the relative correction matrix to obtain a correction matrix, and correcting the contrast inhomogeneity caused by the receive sensitivity in the set of signal intensity images by calculating a ratio of the set of signal intensity images by the correction matrix.

It should be understood that the receive sensitivity (or receive coil sensitivity map, receive coil profile, etc.) can be estimated by any known technique. For example, the receive sensitivity can be estimated from the set of signal intensity images and/or phase images or from electromagnetic field measurement. Additionally, the relative correction matrix can be normalized to a predetermined value, for example, a value that keeps SNR or CNR constant before or after the correction.

Optionally, the optimal imaging parameters for reducing the sensitivity of contrast inhomogeneity caused by the non-uniform transmit field include, but are not limited to, a repetition time, flip angle, inversion recovery time, echo space time or resolution.

Optionally, the non-uniform acquisition conditions include, but are not limited to, a non-uniform transmit field, non-uniform static magnetic field or non-linear gradient field. Additionally, at least one of the non-uniform transmit field, non-uniform static magnetic field or non-linear gradient field are caused by at least one of a coil configuration, wave behavior, tissue susceptibility, B0 shimming or eddy current, for example.

Optionally, the receive sensitivity is estimated using at least one of a set of signal intensity images and/or phase images or electromagnetic field measurement.

In summary, described herein are methods and systems where imaging parameters are iteratively modified and optimized to maximize CNR, with the initial inputs estimated using numerically simulated signal intensities and contrasts. K-space strategies are determined by numerical simulations based on maximizing contrasts and minimizing artifacts, and then optionally modified and confirmed using in vivo experiments. RF system is optionally calibrated to reduce the error and variability caused by different hardware conditions. Moreover, the contrast inhomogeneity caused by both transmit field and receive sensitivity can optionally be corrected.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

DETAILED DESCRIPTION

Figure 1:
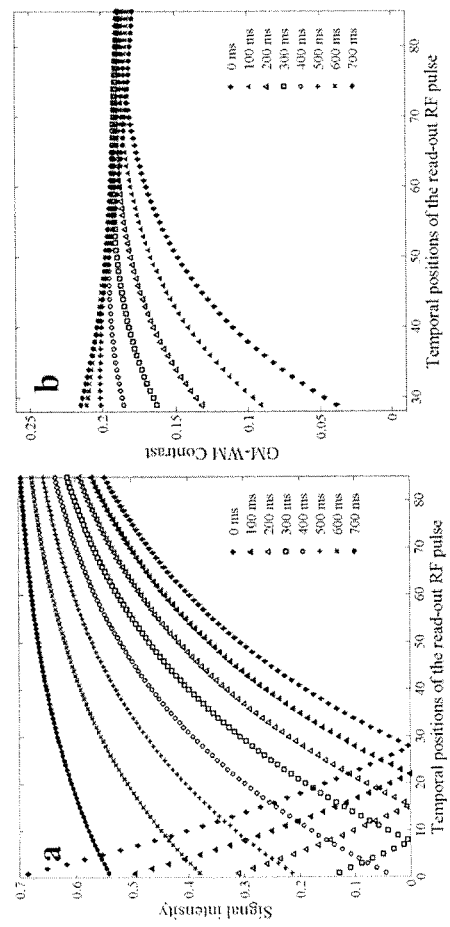
FIG. 1 illustrates simulated signal intensity of the cerebrospinal fluid (CSF) (a) and gray matter-white matter (GM-WM) (b) contrast for different positions of the $i^{th}$ read-out RF pulse at different time intervals (TIs).

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. While implementations will be described for optimizing k-space strategies and/or imaging parameters and correcting image inhomogeneity with regard to MRI modalities, it will become evident to those skilled in the art that the implementations are not limited thereto, but are applicable to other image modalities such as, computed tomography, for example. Additionally, this disclosure contemplates that MRI modalities include MRI techniques with administration of contrast agents, for example, contrast enhanced MR angiography. This disclosure contemplates that the images obtained using the techniques described herein can be directly employed in at least one of diagnosing diseases, monitoring therapy responses, conducting treatment plan, and improving quantification of MRI. For example, the techniques described herein can be used for the diagnoses of specific diseases such as the standardization of the MRI protocol in The Alzheimer's Disease Neuroimaging Initiative. Additionally, the techniques described herein are optionally applicable to a group of individuals in a similar path-physiological situation.

Early methods for optimizing imaging parameters focused on maximizing SNR, which resulted in SNRs far in excess of what is required to detect pathologies being investigated in current clinical MRI systems. In most cases, the contrast between normal and disease tissues, not the SNR, is a better metric for diagnostic sensitivity and specificity of the disease. One main goal for optimizing imaging parameters can therefore be maximizing tissue contrast, or contrast-to-noise ratio (CNR) and/or CNR efficiency instead of SNR. Generally, imaging parameters are usually iteratively optimized through experimentation with multiple scans of a subject. Because the process is very time-consuming and cost-intensive, particularly in the case with very long acquisition times, the experimental approach is usually not practical in clinical settings. In the techniques described herein, signal intensities for interested tissues are numerically estimated, for example, using Bloch equations with tissue MR parameters that are either measured or obtained from the literature. The initial optimized image parameters are determined based on maximizing tissue contrasts and minimizing artifacts as well as noise. The optimized imaging parameters are refined using actual measurements from in vivo experiments based on the initial optimized image parameters.

For example, MR images are reconstructed by an inverse 2D or 3D fast Fourier transform (FFT) from raw data, which are collected in the spatial frequency domain (the "k-space"). Optimal k-space strategy, including sampling trajectory and order, is a critical component in enhancing image quality. Sampling trajectory, closely relate to the point spread function (PSF) of the imaging system, can be used to evaluate image artifacts. Image contrast can be enhanced by optimizing sampling order. It is known that k-space zero line sampling is one of the major factors that determine image contrast. If each k-space line corresponds to the same contrast, for example in FLASH sequence acquisition, k-space zero line filled with any acquired k-space line will not change image contrast. If each k-space line corresponds to a different contrast, k-space zero line filled with different acquired k-space lines will lead to different image contrasts. In most cases, the operator may not be able to ascertain the suitability of a sampling trajectory and order without an unduly large number of trials. According to techniques described herein, optimization of k-space strategies is performed using numerical simulations, with great savings on time and costs.

MRI protocol optimization is important not only for image quality improvement and artifact reduction, but also for reducing the variability of images acquired across different sites and different time points in longitudinal studies. The latter is crucial for increasing statistical power and reducing the number of required subjects in MR studies. It is well known that hardware condition strongly affects the variability of MR images. It is common practice to adjust the strength of the transmitted RF excitation field and the gain of the RF receiver to ensure that the RF excitation pulses have the optimal frequency, strength and duration to evoke the desired MR signal before the commencement of each MR scan. However, this does not necessarily mean that the hardware condition will be stable over time, while in practice, it most likely varies longitudinally. Thus, daily, monthly and annual quality assurance of MR scanner can be done according to the requirements of American College of Radiology. Even with same parameters, big variability in image quality may still exist, due to various factors such as machine-specific static magnetic field inhomogeneity, and different gradient and RF coil systems. For example, previous studies found that transmit field inhomogeneity can be as large as 15%, and the RF calibration factor, defined as the ratio between the actual flip angle and flip angle specified by the operator during the scan, is about 0.80 for the SIEMENS 32-channel head coil in human brain imaging using the SIEMENS MAGNETOM TRIO of SIEMENS AG of MUNICH, GERMANY. Transmit field inhomogeneity can introduce about 15% variation in flip angle across the brain. In addition, RF calibration factor can introduce a 20% system error between the theoretical and real flip angles. Thus, according to the techniques described herein, the RF system is calibrated to reduce system errors.

Moreover, inhomogeneous contrast is also an important factor in voxel-based morphometry (VBM) analyses because it will affect the qualification at tissue boundaries when the tissue classification algorithm takes partial volume effects into account. It is not corrected by general post-processing methods. Contrast inhomogeneity partly results from spatially varying $T_1$ and inhomogeneous transmit field. It should be understood that it is difficult to correct CNR inhomogeneity, and therefore, few works on this subject have been performed. According to techniques described herein, contrast inhomogeneity is reduced or eliminated by both the optimal choice of FA and measured receive sensitivity.

Three types of imaging parameters are defined herein: (1) Theoretical parameters are defined as the parameters obtained from theoretical analysis and simulations; (2) Nominal parameters are those input by the operator to acquire the images, and (3) Real parameters are the actual parameters realized in the imaging process, which can be estimated from experimental data. Ideally these three types of parameters are identical, but in real-world applications, they are not always the same. Unlike subject-independent parameters (e.g., repetition time (TR) and echo time (TE)), flip angle (FA) is subject-dependent, that is, there may exist big differences between its real and nominal values across human brains. The difference can cause inconsistent image quality across subjects, sites and time. To be consistent, FA can be calibrated as shown by the equation below.

$$\alpha_{real} = k \cdot \alpha_{nominal}$$

where $\alpha_{nominal}$ is the optimized nominal FA. k is called calibration factor and is a constant when FA<240°. k is estimated from the slopes of the average real FA vs. nominal FA curves. $\alpha_{nominal}$ can be estimated, for example, using the double flip angle method.

As described above, the techniques described herein can be used for optimizing any MR sequence. Very high quality structural images are required for diagnosis and research. Additionally, the sequences for structural imaging are the most popular sequences in both clinical and research settings. Thus, optimizing the structural imaging sequences are provided as examples only. In other words, the examples focus on the optimization of two popular sequences for structural images (e.g., MP-RAGE and FLASH), but this disclosure contemplates that any MR sequence can be used.

MP-RAGE Sequence

The MP-RAGE sequence is composed of 3D-inversion recovery a and N equally-spaced readout RF pulses of flip angle θ and echo spacing τ. Repetition time TR is defined as the time interval between two successive inversion recovery pulses as shown by Eq. 1 below.

$$TR = TI + N \cdot \tau + TD, \quad (1)$$

where τ is echo spacing time, N is the total number of readout RF pulses, TI is the time interval between the inversion recovery pulse and the first RF readout pulse, and TD is delay time. In order to simplify the formula for signal intensity, $\gamma = \exp(-TI/T_1)$, $\delta = \exp(-\tau/T_1)$, $\rho = \exp(-TR/T_1)$, $\phi = \exp(-TD/T_1)$, and $\mu = \delta \cdot \cos(\theta)$ are defined. For successive excitations in the MP-RAGE sequence, signal intensity from the $i^{th}$ read-out pulse is given by Eq. 2 below.

$$S_i \propto M_i^- \cdot \sin(\theta) = \qquad (2)$$
$$M_0 \cdot \sin(\theta) \cdot \left\{ \frac{(1-\delta)|1-\mu^{i-1}|}{1-\mu} + (\mu)^{i-1} \cdot (1-\gamma) - \gamma \cdot \mu^{i-1} \cdot \frac{M_{eq}}{M_0} \right\}$$

where the steady state magnetization $M_{eq}$ after several TRs is given by Eq. 3 below.

$$M_{eq} = \frac{1 - \varphi + \frac{\varphi \cdot \cos(\theta) \cdot (1-\delta)|1-\mu^{N-1}|}{1-\mu} + \varphi \cdot \cos(\theta) \cdot \mu^{N-1} + \rho \cdot \cos(\alpha) \cdot \cos^N(\theta)}{(1 - \rho \cdot \cos(\alpha) \cdot \cos^N(\theta))} \cdot M_0, \quad (3)$$

The white matter (WM) and gray matter (GM) contrast from the $i^{th}$ read-out RF pulse is given by Eq. 4 below.

$$Con_{i,WM-GM} \propto s_{i,WM} - s_{i,GM}, \quad (4)$$

where $s_{i,WM}$ and $s_{i,GM}$ are the signal intensities of WM and GM, which can be calculated using Eq. 2 with the longitudinal relaxation times and protein densities of WM and GM, respectively. In Eq. 4, GM-WM contrast is a function of N, TI, τ, θ and the temporal position of the read-out RF pulse. Generally, the smaller the acquisition bandwidth is, the higher SNR and CNR are. A small acquisition bandwidth will introduce a large τ. In the MRI scanner used in examples, i.e., SIEMENS MAGNETOM TRIO of SIEMENS AG of MUNICH, GERMANY with Software: NUMARIS/4 Version: Syngo MR B17 DHHS (the "example scanner" as used herein), the largest τ of 10.1 ms corresponds to the smallest bandwidth of about 140 Hz/pixel for the MP-RAGE sequence. For τ of 10.1 ms, the simulation suggests that the optimal FA should be 12°. N is usually determined by the size of the image coverage (e.g., whole brain) and slice resolution. The read-out RF pulse used to fill the k-space center is determined by k-space sampling order. It should be understood that, for a sequence in a commercial scanner such as the example scanner, the k-space strategy, including k-space trajectory and sampling order, may be fixed by a given setting. Thus, the temporal position of the RF pulse that lead to maximum GM-WM contrast of a simulated image acquired with the MP-RAGE sequence at 3.0 Tesla was first computed using computer simulations without considering the pre-determined scanner settings. Then, the optimal k-space sampling for settings that can be realized on the commercial scanner were determined.

Although it is a property in the image domain that is determined by all Fourier components in the entire k-space, contrast between WM and GM is mostly determined by k-space center which are associated with the low spatial frequency components in k-space. According to Eqs. 2-4, GM and WM contrast from the $i^{th}$ read-out RF pulse is a function of the temporal position of the RF pulse and the total number of read-out RF pulses N. The major objective of k-space optimization is to optimize the k-space trajectory such that k-space center has the maximal $Con_{i,WM-GM}$. As described above, because the example scanner has a few fixed k-space sampling settings, it was not possible to reach the theoretically optimal k-space sampling for MP-RAGE in experiments. Instead, the k-space sampling was optimized for the available settings on the example scanner.

Simulation of Optimized Imaging Parameters

Effects of the major imaging parameters (e.g., number of readout RF pulses, flip angle, τ, TI, and TD) were simulated using Bloch's equations based on the values of $T_1$, $T_2$, and proton density of the WM, GM and CSF of the human brain, which at 3.0 T are 1400/850/3500 ms, 100/90/300 ms, and 0.75/0.65/1.0, respectively. Relaxation effects during RF excitation were neglected and perfect spoiling of transverse magnetization was assumed after each inversion pulse and before each excitation pulse. Signal intensity and contrast of brain tissues were respectively simulated using Eqs. 2 and 4 using MATLAB of MATH WORKS, INC. of NATICK, Mass. Optimal imaging parameters were determined based on simulation results and validated by in vivo experiments.

In the simulations, $\tau$ was limited by the hardware (e.g., the example scanner's acquisition bandwidth and pulse duration time) and total scan time. On the example scanner, the largest $\tau$ of 10.1 ms corresponds to the smallest bandwidth of about 130 Hz/pixel for the MP-RAGE sequence. Setting $\tau$ to 10.1 ms, the effect of FA on signal intensities and tissue contrasts was simulated using Eq. 4 to find the optimal FA. At the optimal FA, signal intensities of GM and WM, and GM-WM contrast were computed as functions of the number of readout RF pulses for different TIs. The functional relationship between GM-WM contrast and TI was simulated to obtain the optimized TI. Finally, GM, WM and CSF signal intensities vs. different TDs were simulated to find the optimized TD.

Flip Angle (FA) Calibration

As described above, three types of imaging parameters are defined: (1) Theoretical parameters are defined as the parameters obtained from theoretical analysis and simulations; (2) Nominal parameters are those input by the operator on the MR system to acquire images, and (3) Real parameters are the actual parameters realized in the imaging process. As for subject-independent parameters (e.g., TR and TE), these three types of parameters are always identical. However, this is not true for subject- and/or position-dependent parameters. For example, FA is subject-dependent and position-dependent. Therefore, there may be differences between real and nominal FA values across different brains and across different regions of a brain. These difference can cause inconsistent image quality across subjects, sites and/or over time. To reduce the inconsistency, FA can be calibrated using measured flip angle maps as shown by Eq. 5 below.

$$\alpha_{real} = k \cdot \alpha_{nominal} \tag{5}$$

where $\alpha_{nominal}$ is the optimized nominal flip angle. k is called the calibration factor. k is a constant when FA<240° and can be estimated from the slopes of the real FA versus nominal FA curves. The real FAs corresponding to nominal FAs of 60° and 120° were estimated using the double flip angle method. The calibration factor k was estimated based on the linear relationship between the real and nominal FAs using Eq. 5.

Image Quality Evaluation

In order to quantitatively evaluate image quality, SNR and CNR efficiencies are introduced to evaluate the quality of the images acquired with different imaging parameters because both SNR and CNR are functions of total scan time. The SNR efficiency, $SNR_{eff}$, defined as SNR per square root total scan time TA, is given by Eq. 6 below.

$$SNR_{eff} = SNR / \sqrt{TA}, \tag{6}$$

A single type of tissue may have different signal intensities because of signal inhomogeneity caused by non-uniform transmit field and receive sensitivity. Thus, SNR of the single tissue cannot be used to evaluate the image quality. Instead, global SNR was used as an indicator to evaluate the image quality, avoiding the error caused by signal inhomogeneity.

Similarly, the CNR efficiency is defined as CNR per square root total scan time TA as given by Eq. 7 below.

$$CNR_{eff} = CNR / \sqrt{TA}, \tag{7}$$

In order to avoid effects of image inhomogeneity, contrasts between nearby tissues were used to assess image quality. Noise and artifact level were determined by subtracting two images acquired with identical imaging parameters at different times.

Results

As shown in Eq. 4, GM-WM contrast is a function of N, TI, $\tau$, $\theta$ and the temporal position of the read-out RF pulse. Generally, the total number of RF pulses N is related to the spatial resolution along the slice direction. In vivo experiments confirmed that N was chosen to be 176 for whole brain coverage at a slice thickness of 1 mm on the example scanner. To simplify the problem, N=176, FA=12° and $\tau$=10.1 ms were set in the example optimization. FA=12° was chosen based on simulation results shown below. The same procedure can be used for different Ns, FAs, and $\tau$s. FIG. 1 shows the simulated signal intensity of the CSF and GM-WM contrast as a function of the temporal position of the read-out RF pulse for different TIs. The SNR of the CSF is illustrated because the signal intensity of the CSF is the lowest among the major brain tissues (CSF, GM and WM) in $T_1$-weighted images acquired with the MP-RAGE sequence. If the SNR of the CSF is acceptable, the SNRs of the GM and WM would be acceptable. When the temporal position of the read-out RF pulse is more than 30, the signal intensity of the CSF increases monotonically with increasing TI and the temporal position of the readout RF pulse as shown in FIG. 1a. $i_{max}$ is defined as the temporal position of the read-out RF pulse that corresponds to the maximum GM-WM contrast. FIG. 1b shows that $i_{max}$ shifts to lower values with increasing TI. It is in general not equal to half of the total number of readout RF pulses: for example, it is 80 but not 88 when TI=0. That is, the center of the readout RF pulse does not necessarily lead to maximal GM-WM contrast. GM-WM contrast increases but the $i_{max}$ decreases with increasing TI. When the tradeoff between GM-WM contrast and CSF signal intensity is taken into account, the theoretical $i_{max}$ should be in the range from 30 to 80 for the various TIs. In general, for fixed FA and $\tau$, the GM-WM contrast is a function of N, TI, and the temporal position of the read-out RF pulse; $i_{max}$ is a function of N and TI. For a fixed N, $i_{max}$ is a function of TI.

Although the example scanner limits the k-space center to the center of the read-out RF pulses, it is possible to shift k-space center by slice partial Fourier factors, which can be set as off (e.g., 1), 7/8, and 6/8. When the nominal N is 176, slice partial Fourier factors of off, 7/8, and 6/8 correspond to real Ns of 176, 156, and 132, respectively. In that case, k-space center acquisition on the example scanner is respectively set to be the $88^{th}$, $66^{th}$ and $44^{th}$ read-out RF pulse. In the examples, k-space sampling is optimized among the available settings on the example scanner by determining the optimal partial Fourier setting. The pre-set read-out RF temporal position may not necessarily equal to $i_{max}$.

Figure 2:
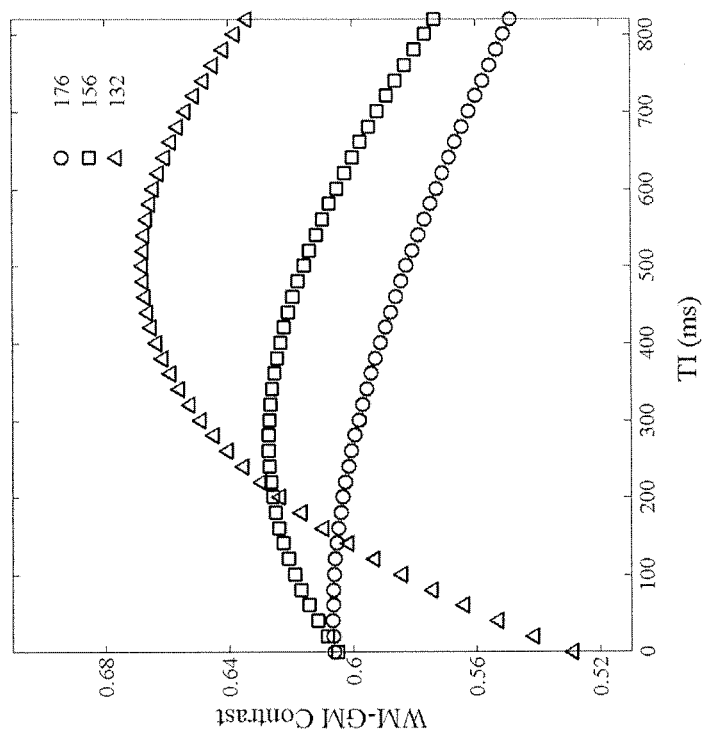
FIG. 2 illustrates simulated contrast between the GM and WM as functions of TI at number of readout RF pulses of 176, 156, and 132 at an interval time between readout RF pulses of 10.1 ms and flip angle of 12°.

As described above, due to scanner limitations, experiments could not be conducted with the theoretically optimal $i_{max}$. Instead, further simulations and experiments were limited to the settings that can be achieved on the example scanner. In other words, the choice of real N associated with a nominal N and the temporal position of k-space center are fixed on the example scanner. TI can only vary freely to obtain maximum GM-WM contrast under the constraints of the example scanner. Computer simulations were used to find the optimal TI, $TI_{max}$, that produces the maximal GM-WM contrast. In the example scanner, k-space center is given at $88^{th}$, $66^{th}$ and $44^{th}$ for a nominal N of 176 with slice partial Fourier of off, 7/8, and 6/8. The simulated GM-WM contrast vs TI curves for different real Ns and corresponding k-space centers are shown in FIG. 2. $TI_{max}$ for real N of 176, 156, and 132 were around 50, 300, and 500 ms, respectively. The peaks in the CNR vs TI curves are relatively flat in FIG. 2. In the MP-RAGE sequence, the effective inversion recovery time $TI_{eff}$ is defined as the time interval between the inversion recover pulse and the RF read-out pulse for k-space center. Generally, the readout RF pulse corresponding to $i_{max}$ should be used to fill k-space center because k-space center is a major determining factor of image contrast. Therefore, the optimal $TI_{eff}$ is given by Eq. 8 below.

$$TI_{eff} = TI_{max} + i_{max}\tau. \quad (8)$$

On the example scanner, the theoretical $i_{max}$ cannot be achieved. Instead, the pre-set k-space center can only be used. Thus, $i_{max}$ in Eq. 8 was replaced with the actual temporal position of the RF-pulse for k-space center and calculated $TI_{eff}$ using Eq. 8. The optimal $TI_{eff}$ values are 940, 967, and 945 for real Ns of 176, 156 and 132, respectively. It is almost constant for the different real Ns. However, both real N and k-space center strongly affected WM-GM contrast. The WM-GM contrast when real N is 132 and the k-space center is filled with the $44^{th}$ RF read-out pulse was 10% more than that when real N is 176 and k-space center is filled with the $88^{th}$ RF read-out pulse.

Figure 3:
FIG. 3 illustrates human brain images acquired at an interval time between readout RF pulses of 10.1 ms and flip angle of 12°, effective inversion recovery time of 950 ms, total readout RF pulse of 176, and slice partial Fourier factors of 1 (a), and 6/8 (b).

In order to validate the simulation, brain images were acquired without slice partial Fourier (FIG. 3a) and with a slice partial Fourier factor of 6/8 (FIG. 3b). The other acquisition parameters, including $TI_{eff}$, were identical. The results demonstrated that both the SNR and CNR of the brain images acquired with a slice partial Fourier factor of 6/8 were about 10% higher than those acquired without slice partial Fourier. The results from the in vivo experiments are in good agreement with the simulation results in FIG. 2. Therefore, the optimal real N and k-space center were chosen to be 132 and the $44^{th}$, respectively, among the realizable settings of the example scanner.

Figure 4:
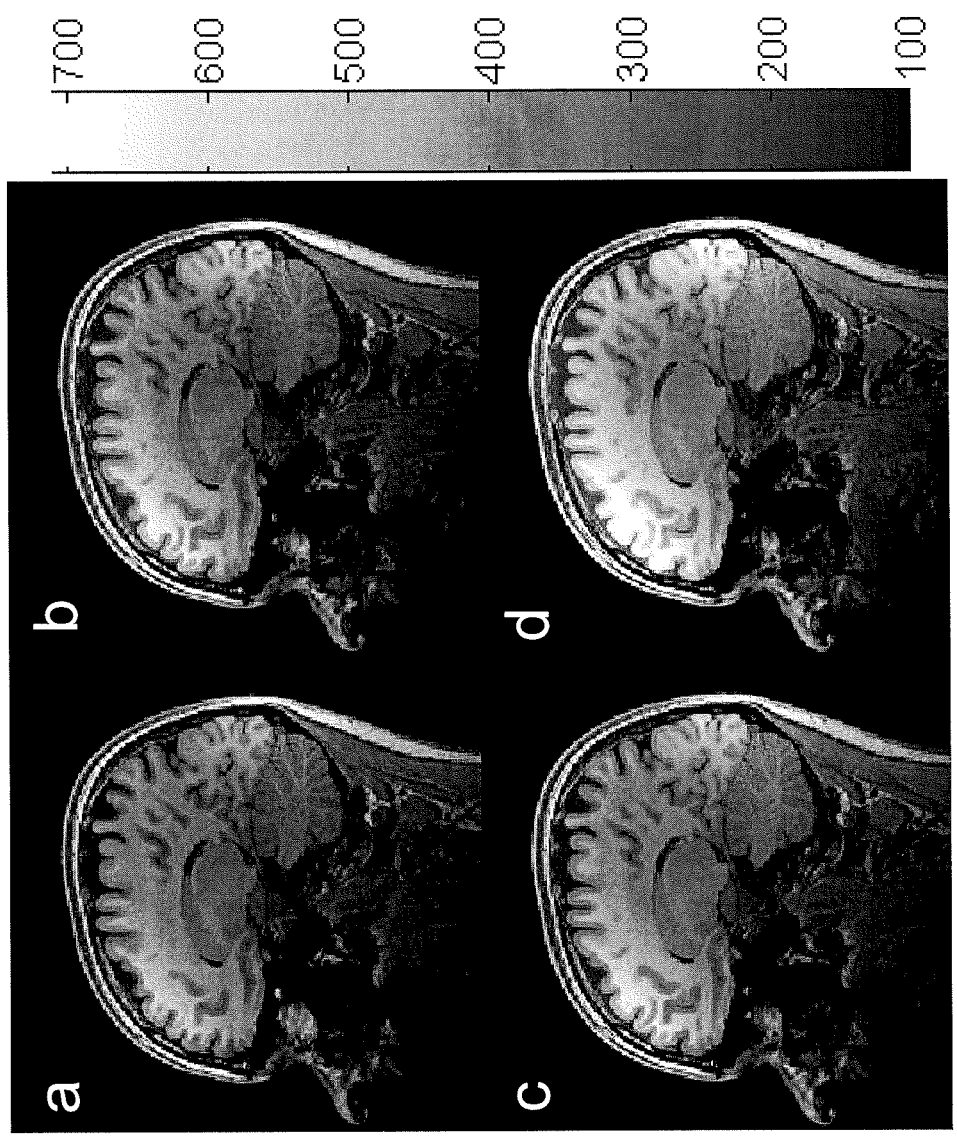
FIG. 4 illustrates in vivo brain images acquired using the MP-RAGE sequence with different effective inversion recovery times $TI_{eff}$: 900 ms (a), 950 ms (b), 1020 ms (c) and 1100 ms (d) at a flip angle of 12°, an interval time between readout RF pulses of 10.1 ms, and slice partial Fourier factor of 6/8.

FIG. 4 shows in vivo brain images acquired using the MP-RAGE sequence with different $TI_{eff}$s: 850 (a), 950 (b), 1000 (c) and 1200 (d) ms at a flip angle of 12°, with a slice partial Fourier factor of 6/8. The results indicated that the average signal intensity of brain tissues increased from 361 to 421 (around 10%) when $TI_{eff}$ increased from 850 to 1200 ms. The maximum GM-WM contrast occurred at a $TI_{eff}$ of 980 ms. After k-space trajectory optimization, the change in CNR was less than 4% when TI increased from 850 to 1200 ms, in agreement with the simulation results in FIG. 2. To maximize CNR efficiency, the optimal choice of $TI_{eff}$ should be short because short $TI_{eff}$ reduces scan time. Thus, the optimal $TI_{eff}$ was set at 950 ms.

Figure 5:
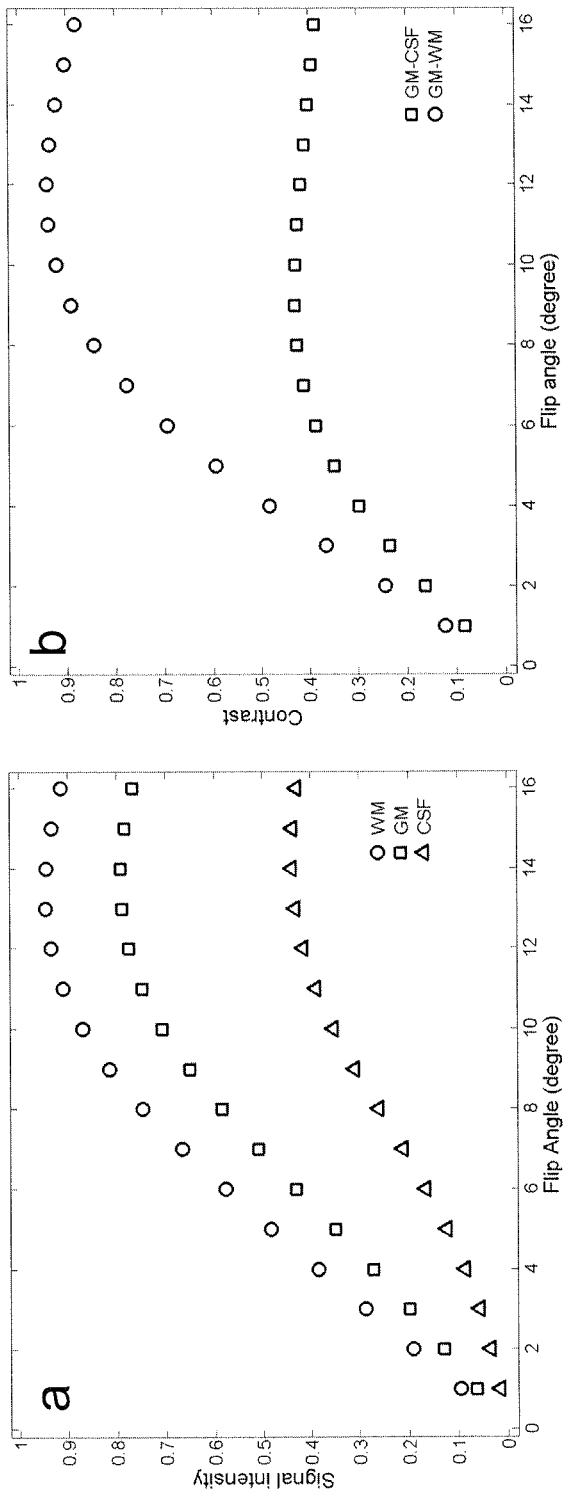
FIG. 5(a) illustrates relationships between simulated signal intensities of brain tissues (e.g., the GM, WM and CSF) and flip angle at an interval time between readout RF pulses of 10.1 ms.
FIG. 5(b) illustrates relationships between simulated contrasts of brain tissues (e.g., WM-GM, and GM-CSF) and flip angle using an example optimal k-space trajectory.

The simulated effects of FA on GM, WM and CSF signal intensities and contrasts between the GM and WM and between the GM and CSF at $\tau = 10.1$ ms are shown in FIG. 5. Both signal intensities and contrasts first increased and then decreased with increasing FA. Signal intensity reached its maximum at FA around 10° for the WM, and around 13° for the GM and CSF. After reaching their maximum values, signal intensities declined slightly with increasing FA. The contrasts started to approach their asymptotic values at FA around 8°, reaching their maxima at FA around 10° and declining slightly at FA around 12°. The contrast curve was almost flat when FA increased from 10° to 12°. That is, inhomogeneous FA would have a small impact on the contrast when FA is in the range from 9 to 14°. The signal intensities and contrasts reached their maximum values at different FAs. Since maximizing CNR is more important than maximizing SNR for diagnosis and tissue segmentation, the optimal FA was chosen to be 12°. With this FA, GM-WM contrast achieved maximal values and was insensitive to non-uniform FA in different regions of the brain or across brains.

Figure 6:
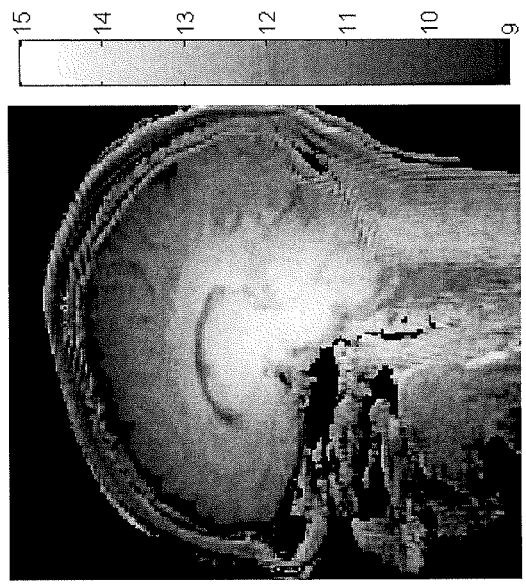
FIG. 6. illustrates an estimated image of the actual flip angles of a nominal flip angle of 12° using double flip angle method.

The real FA for a nominal FA of 12° was determined based on the estimated real FA values for nominal FAs of 60° and 120° because the relationship between the real and nominal FAs is linear (FIG. 6). The real FAs were estimated using the double flip angle method at nominal FAs of 120/60° for which the error of the estimated real FAs was minimized. The maximum variation across different parts of the human brain was around 1.0° for a nominal FA of 12°. Inhomogeneous transmit field introduced less than 10% FA variation. The variation led to significant signal intensity changes (FIG. 1a), but only slight contrast changes (FIG. 1b). As for the ten subjects in the example study, the average real FA was 12°±0.3°. The variation of FA across the ten subjects was less than 3% (0.3/12). The average calibration factor k (Eq. 6) for the ten subjects was 0.98±0.002. The result indicated that the real FA was close to the nominal FA for the example scanner. Their difference was around 2%. The variation of the calibration factor k across subjects, 0.2% (0.002/0.98), was small. Thus, it was not necessary to consider the effect of individual differences on the calibration factor for the example scanner.

Figure 7:
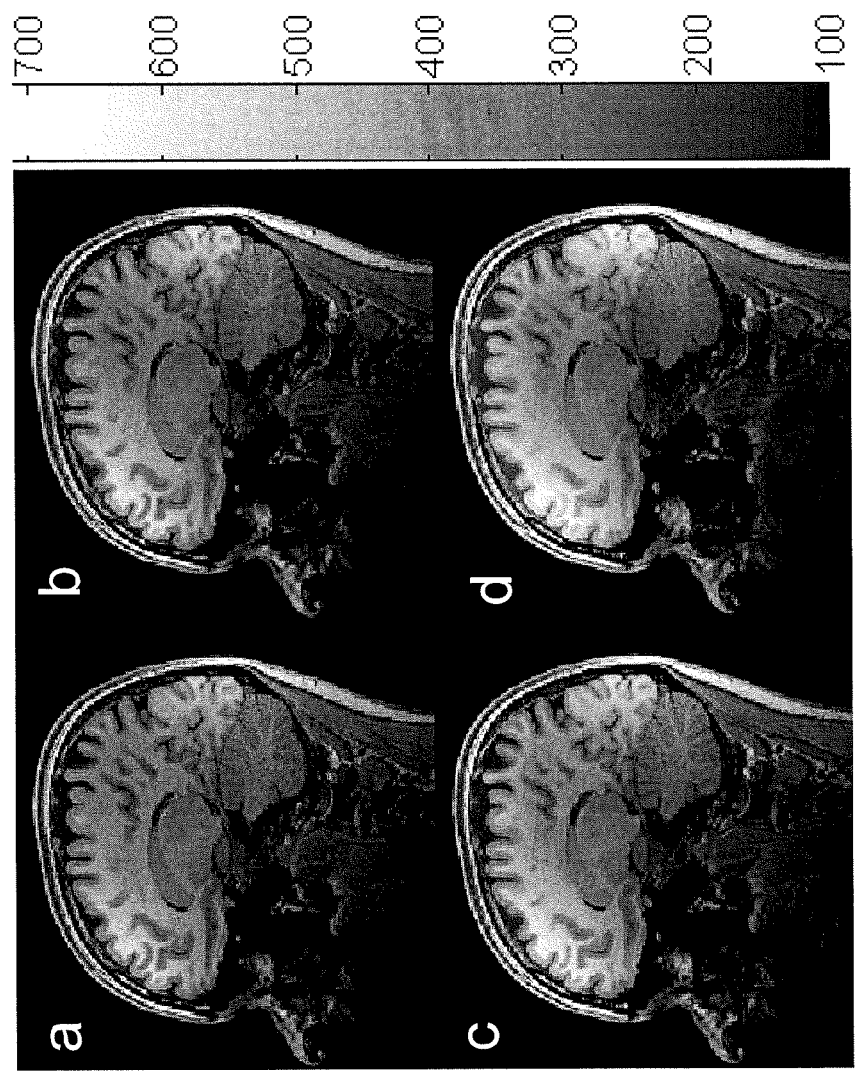
FIG. 7 illustrates in vivo brain images acquired using the MP-RAGE sequence with different flip angles: 9° (a), 11° (b), 12° (c), and 14° (d) with $\tau/TI_{eff}/TR=10.1/950/1950$ ms.

FIG. 7 shows in vivo brain images acquired using the MP-RAGE sequence at TIeff of 950 ms with different flip angles: 9° (a), 11° (b), 12° (c) and 14° (d). ROI analysis indicated that with increasing FA, SNRs of the GM and CSF increased, while SNR of the WM increased only when FA was less than 10° and started to decrease when FA was more than 10°. The averaged SNR of brain tissues increased approximately 15% with increasing FA from 9° to 12°. The maximal contrast between the GM and WM occurred at the FA of 12°. These results were completely consistent with the simulation results in FIG. 5.

Figure 8:
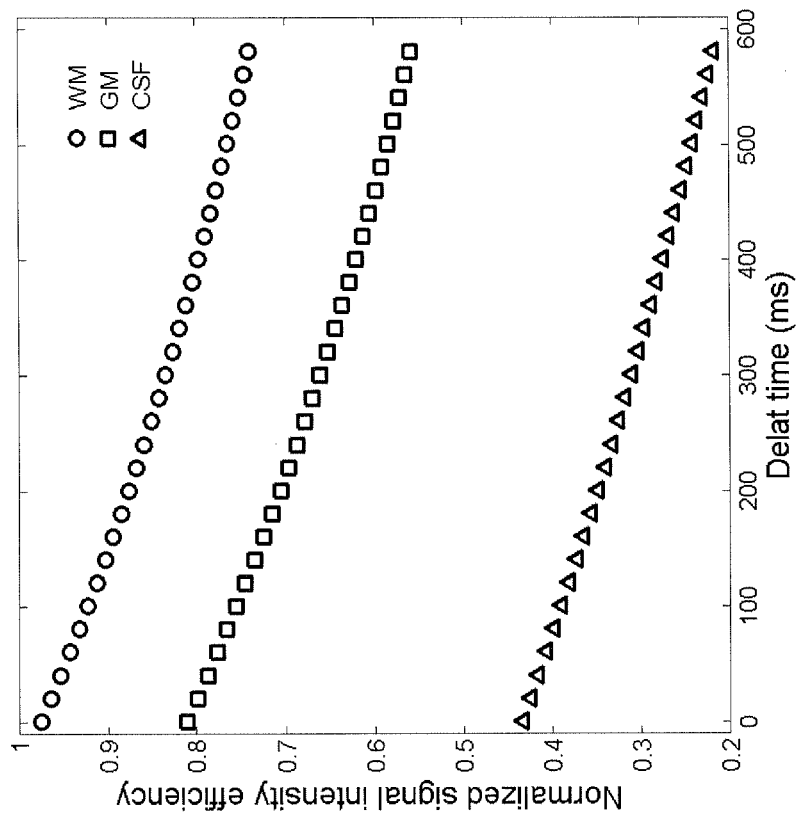
FIG. 8 illustrates simulated signal intensities of the GM, WM and CSF at different delay times (TD) at the optimal TN of 132 and k-space trajectory.
Figure 9:
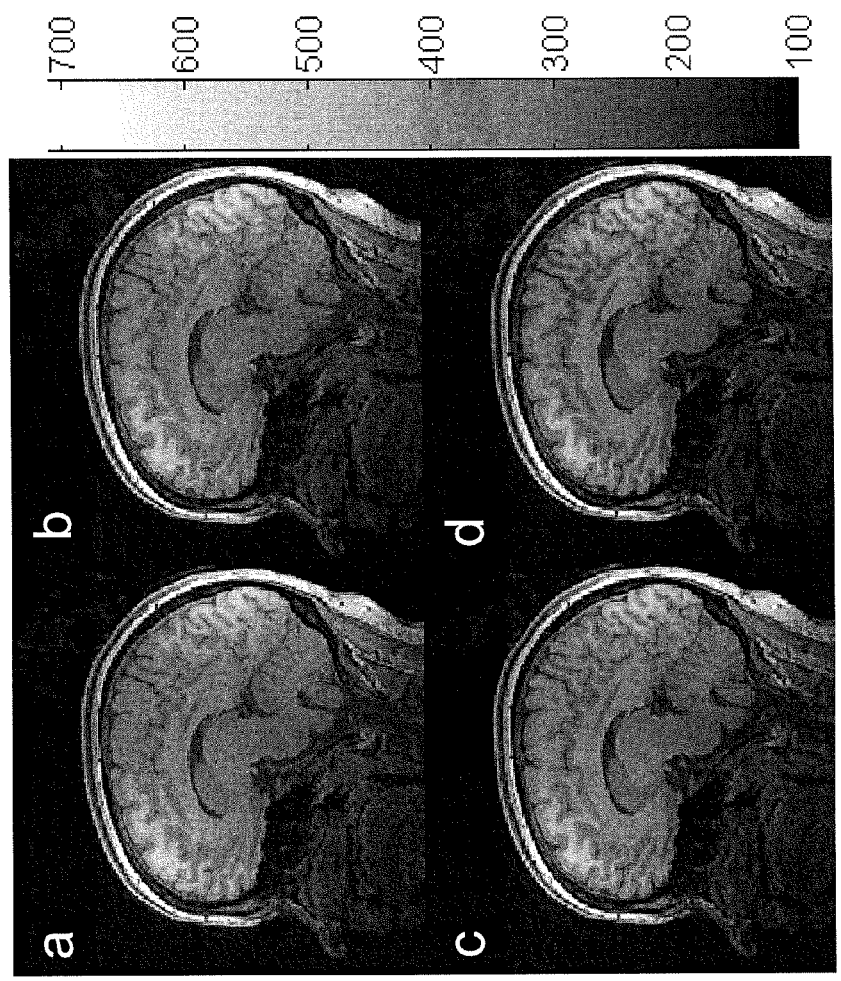
FIG. 9 illustrates in vivo brain images acquired using the MP-RAGE sequence with different delay times (TD): 0 ms (a), 100 ms (b), 200 ms (c), and 400 ms (d).

The relationship between signal intensities of brain tissues and TD is shown in FIG. 8. All signal intensities of major brain tissues (WM, GM and CSF) decreased with increasing TD. Additionally, the contrasts among these brain tissues increased slightly with increasing TD. In vivo brain images acquired using the MP-RAGE sequence with TD of 0 (a), 100 (b), 200 (c), and 400 ms (d) are shown in FIG. 9. ROI analysis showed that the SNRs of all brain tissues decreased around 18% when TD increased from 0 to 400 ms. On the other hand, the CNR remained around 38 with increasing TD. The results from the in vivo experiments agreed extremely well with the simulations.

Figure 10:
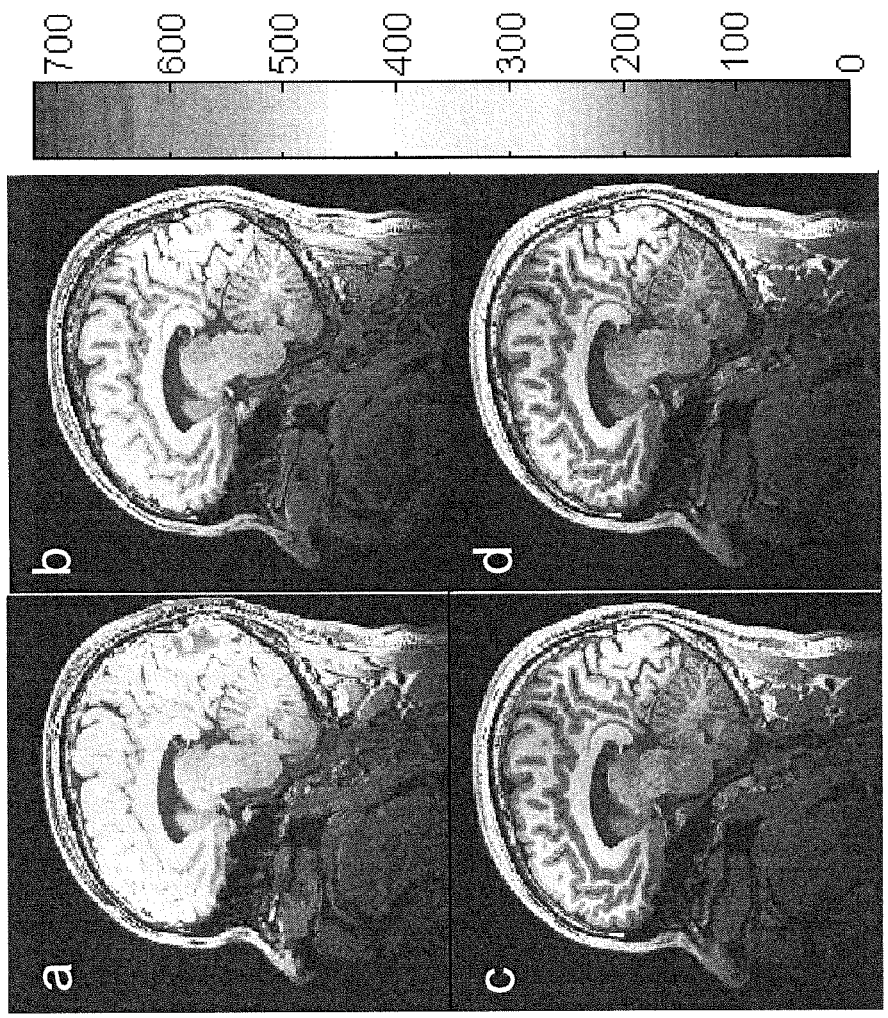
FIG. 10 illustrates in vivo brain images acquired using the MP-RAGE sequence with different imaging parameters: optimized parameters (a), SEIMENS default parameters (b), recommended by Harvard University in FreeSurfer (c) and Alzheimer's Disease Neuroimaging Initiative (ADNI) (d).
Figure 11:
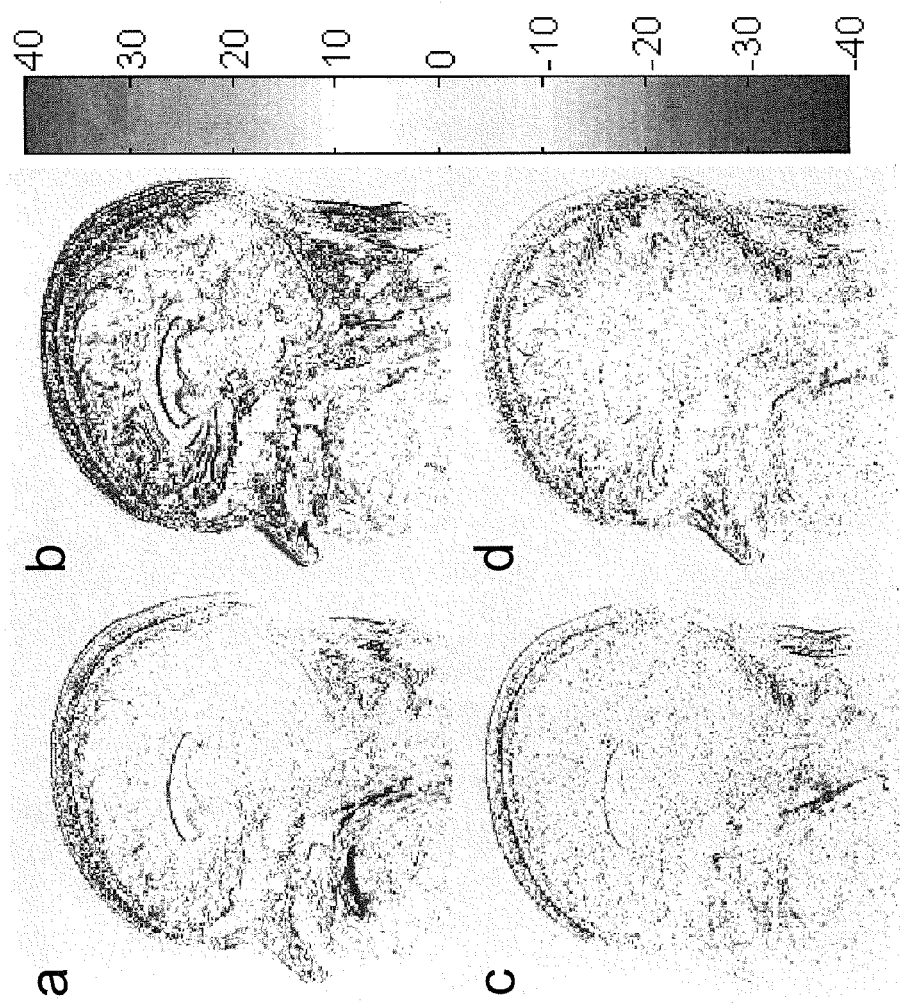
FIG. 11 illustrates the noise and artifact distribution of in vivo brain images acquired using the MP-RAGE sequence with different imaging parameters: optimized parameters (a), SEIMENS default parameters (b), recommended by Harvard University in FreeSurfer (c) and Alzheimer's Disease Neuroimaging Initiative (ADNI) (d).

In order to evaluate the performance of the optimization procedure, the quality of the images acquired using the optimal setting were compared with those acquired using imaging parameters recommended by Siemens, ADNI and Free-Surfer. The ranking of image signal intensity and GM-WM contrast (from the highest to the lowest) is: the optimal imaging parameters (FIG. 10a)>recommended parameters in FreeSurfer (FIG. 10b)>Siemens default (FIG. 10c)>ADNI (FIG. 10d). Quantitative analysis indicated that the mean signal intensity and WM-GM contrast of images acquired with the optimal image parameters was 15% higher than those of images acquired using the recommended parameters in FreeSurfer. To further evaluate these image qualities, the distributions of noises and artifacts corresponding to these imaging parameters were generated by subtracting two images acquired with identical imaging parameters at different time. The ranking in noise and artifacts (from the lowest to the highest) is: ADNI (FIG. 11d)<optimal imaging parameters (FIG. 11a)<recommended parameters in FreeSurfer (FIG. 11b)<<Siemens default (FIG. 11c). However, these noises did not have significant difference. Generally, the noise of image acquired at $\tau$ of 10.1 ms and receive acquisition bandwidth of around 140 Hz/pixel in FIG. 11a will be significantly lower than that of images acquired with recommended imaging parameters in FIG. 11b-d. The reason is because reduced noise caused by receive acquisition bandwidth acquisition is offset by slice partial Fourier acquisition in FIG. 11a. The WM-GM CNR of the images acquired with the optimal image parameters (FIG. 10a) was 15% higher than that of images acquired using the recommended parameters in Free-Surfer (FIG. 10b). The total scan time in the optimal protocol is of 4 minute 16 second; the total scan time in the FreeSurfer protocol is 5 minute 41 second. Thus, the WM-GM CNR efficiency of the optimal protocol is 33% higher than that of the FreeSurfer protocol.

The SNR and CNR of $T_1$-weighted image acquired with the MP-RAGE sequence is sensitive to the variations and values of the real FA. In most cases, the variations can contribute to signal intensity inhomogeneity, strongly affecting the accuracy and precision of voxel-based morphometric quantification and automatic diagnostic analysis. Various factors, such as coil configuration, tissue type and distribution, strongly affect the distribution of the transmit field and RF calibration factor and therefore the real FA. It is desirable to calibrate transmit field for different subjects and coil configurations. FIG. 4 shows that the theoretical FA from the simulation was in good agreement with the nominal and real FAs after RF calibration. The variation of FA across the brain was around 1° for a nominal FA of 12°. The inhomogeneous transmit field caused significant signal intensity variations, but had little impact on the contrasts between brain tissues. If the CNR of two tissues is much greater than the variations of two tissue signal intensities, the two tissues can be distinguished easily. The CNR inhomogeneity does not need to be converted to quantify and segment the two tissues. However, the CNR of two tissues is comparable to or less than their signal intensity variations. The inhomogeneous signal intensity of the two tissues should be corrected to further improve signal inhomogeneity. FA can be calibrated and optimized to maximize CNR and reduced some effects of inhomogeneous transmit field on signal intensity inhomogeneity.

Various factors can affect the difference between the initial optimal imaging parameters and final optimal imaging parameters: (1) In the simulation, perfect spoiling was assumed and relaxation during RF pulses and off-resonance artifacts were ignored. With increasing flip angle, perfect spoiling becomes difficult. As a result, imperfect spoiling affects the accurate estimation of signal intensity and other parameters, such as relaxation time. Further studies of in vivo experiments at different flip angles indicated that artifacts and noise were most or less constant for flip angles from 8 to 14°. If the study objective is to segment brain tissues and quantify their volumes, accurate estimation of signal intensity is not very important. The effect of imperfect spoiling can be ignored. However, imperfect spoiling is problematic if the images acquired at large flip angles are used to estimate relaxation time. In that case, Eq. 2 cannot be used to estimate the relaxation time precisely. (2) The MR parameters of brain tissues, such as relaxation time and proton density, vary across different brain regions of a single subject and across brains of different subjects. The variability was ignored in the simulation; average MR parameters were used to estimate the initial optimized imaging parameters in the simulation. Thus, in vivo experiments should be used to refine the optimal imaging parameters following simulation. In other words, the simulation provided the range of the optimal imaging parameters and shortened the time for the optimization of MP-RAGE sequence. Such simulation provided an excellent tool for MR sequence optimization, reducing the costs of implementing untested prototypes on actual MRI systems.

In comparison to previous MP-RAGE protocols, SNR and CNR were optimized and improved by more than 15% when echo-spacing increased from 8 to 10.1 ms and FA from 9 to 12°, k-space trajectory was optimized and improved CNR by more than 10%, (3) TD was minimized and enhanced the efficiency of MP-RAGE sequence, and (4) the total number of readout RF pulses was reduced using slice partial Fourier and slightly increased SNR and CNR. As a result, an increase in CNR efficiency of around 33% was achieved for the optimization of MRI protocol as shown in FIG. 10a.

FLASH Sequence

The FLASH sequence is composed of a series of N equally-spaced readout RF pulses of flip angle θ and the repetition time. N is the total number of readout RF pulses, TI is inversion recovery time, and TD is delay time. In order to simplify the formula of signal intensity, $\alpha = \exp(-TR/T_1)$, and $\beta = \alpha \cdot \cos(\theta)$. For successive excitations in FLASH sequence, the signal intensity after the $i^{th}$ excitation pulse is given using Eq. 9 below.

$$s_i \propto M_i \cdot \sin(\theta) = M_0 \cdot \sin(\theta) \cdot \frac{(1-\alpha)[1-\beta^{i-1}]}{1-\beta} \cdot S(x). \quad (9)$$

where S(x) is the receive sensitivity of the RF coil, and $M_0$ is the equilibrium magnetization at the location x. It is very difficult to simulate the noise exactly because noise in MRI includes not only white noise but also physiological noise. Additionally, white noise is relatively stable in MR experiments. Thus, it is assumed that noise is dominant and stable at the different imaging parameters in the simulation. The WM-GM CNR efficiency ($CNReff_{WM-GM}$) at a total scan time TA is given by Eq. 10 below.

$$CNReff_{WM-GM}(x) \propto \left[ M_{WM} \cdot \frac{1-\alpha_{WM}}{1-\beta_{WM}} - M_{GM} \cdot \frac{1-\alpha_{GM}}{1-\beta_{GM}} \right] \cdot \sin(\theta(x)) \cdot \quad (10)$$

$$S(x) \cdot \frac{1}{\sqrt{TA}} \propto \left[ M_{WM} \cdot \frac{1-\alpha_{WM}}{1-\beta_{WM}} - M_{GM} \cdot \frac{1-\alpha_{GM}}{1-\beta_{GM}} \right] \cdot$$

$$\sin(\theta(x)) \cdot S(x) \cdot \frac{1}{\sqrt{TR}},$$

where $M_{WM}$ and $M_{WM}$ are the equilibrium magnetization of WM and GM, respectively. $\alpha_{WM} = \exp(-TR/T_{1,WM})$, $\alpha_{GM} = \exp(-TR/T_{1,GM})$, $\beta_{WM} = \alpha_{WM} \cdot \cos(\theta(x))$ and $\beta_{GM} = \alpha_{GM} \cdot \cos(\theta(x))$. $T_{1,WM}$ and $T_{1,WM}$ are the longitudinal relaxation times of WM and GM. The major objective of the optimization procedure is to maximize the contrast between WM and GM and reduce signal inhomogeneity using optimal imaging parameters (TR, θ) at a relatively short scan time. Since receive sensitivity S(x) is relative independent of imaging parameters (excluding receiver gain), it is assumed that sensitivity S(x)=1 in computer simulation of Eq. 10. CNR efficiency (Eq. 10) was used as the objective function to determine the optimal imaging parameters in computer simulations and removed the effect of CNR inhomogeneity CNR (x) on the inhomogeneous FA which is introduced by transmit field. However, in practice, CNR inhomogeneity inhomogeneous receive sensitivity can be taken into account caused by. CNR(x) can optionally be corrected by measured receive sensitivity which is corrected estimated using minimal contrast image method. The corrected $CNR_{corrected}(x)$ is given by Eq. 11 below.

$$CNR_{corrected}(x) \propto CNR(x)/S(x) \quad (11)$$

Simulation

Figure 12:
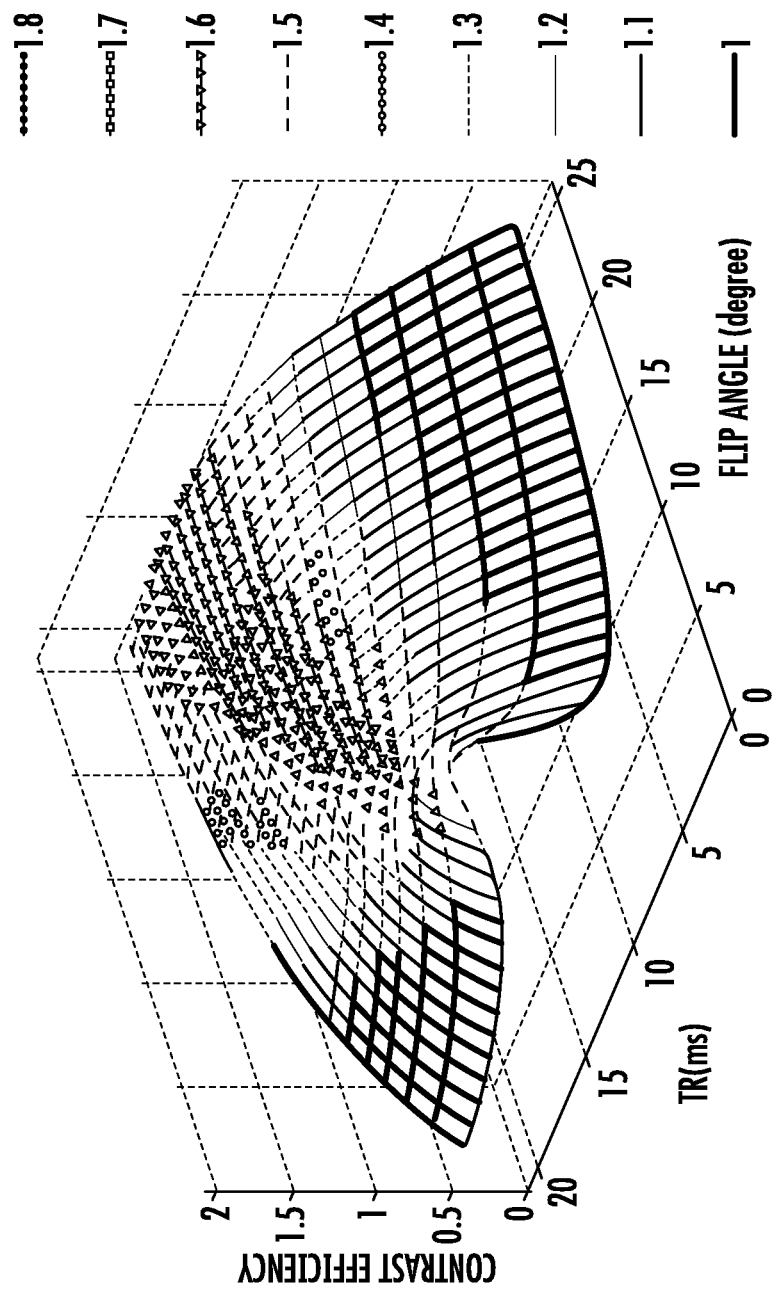
FIG. 12 illustrates dependence of simulated CNR efficiency between WM and GM on both different flip angles and TRs.
Figure 13:
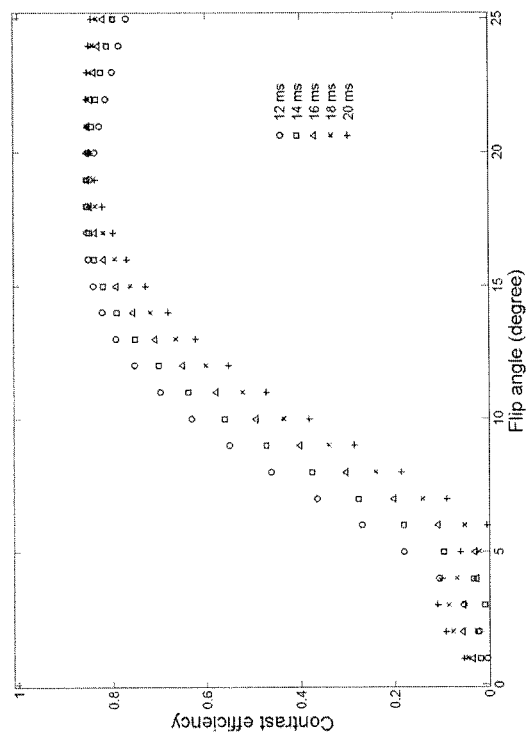
FIG. 13 illustrates dependence of simulated CNR efficiency between WM and GM on flip angles at the TRs of 12, 14, 16, 18, and 20 ms.

After gradient and RF spoiling, complete spoiling of transverse magnetization was assumed to be achieved. MR signal becomes independent of $T_2$, and follows Eq. 9. FIG. 12 shows the dependence of simulated GM-WM contrast efficiency on FA and TR using Eq. 10. The results demonstrate that high GM-WM contrast efficiencies could be achieved with a large range of FAs and TRs. Since multiple settings of TRs and flip angles might be used to achieve high GM-WM contrast efficiency, to reduce total scan time and patient burden, a short TR is preferred. The possible candidate TR and FA could be TR less than 20 ms and FA less than 30°. In order to further refine these two parameters, GM-WM contrast efficiency vs FA was simulated for a range of TRs: 12 TR 18 ms (FIG. 13). The contrast efficiency rapidly increased when FA was larger than 6°, reaching its maximum at FA=16°, TR=12 ms, and then reduced very slowly with increasing FA. When TR increased from 12 to 18 ms, the peak of the GM-WM contrast efficiency vs FA curve shifted from 16° to around 20°. The GM-WM contrast efficiency was almost the same when 15° FA 21° and 12 TR 14 ms. This was a very important result because it suggested that GM-WM contrast efficiency did not depend on FA in this range. Therefore, the impact of transmit field on GM-WM contrast can be greatly reduced or eliminated if the actual FA falls within this range. It is suggested that the optimal TR should be 13 ms, and the optimal FA should be between 16° to 18° based on considerations of the trade-off between scan time and bandwidth, which should be more than 100 Hz/pixel to reduce signal loss. In the examples, the optimal FA was finally chosen to be 17° to achieve maximum contrast efficiency and reduce the sensitivity of GM-WM contrast to FA caused by non-uniform transmit field.

Experimental Results

Figure 14:
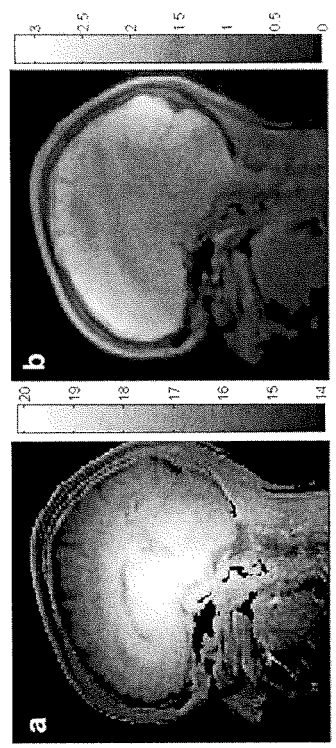
FIG. 14 illustrates flip angle map of brain with a body coil used as a transmitter at a nominal flip angle of 17° (a) and receive sensitivity map (b) with a 32 channel head coil as a receiver.

A method for correcting inhomogeneous contrast in an MRI image is described below. It is first possible to correct for a sensitivity of a contrast inhomogeneity caused by non-uniform acquisition conditions such as a non-uniform transmit field, for example. Other possible non-uniform acquisition conditions include non-uniform static magnetic field or non-linear gradient field. For example, tissue contrast for an MRI sequence can be simulated (e.g., using Bloch equations) and then optimal imaging parameters for reducing the sensitivity of the contrast inhomogeneity caused by the non-uniform transmit field are found. Low-resolution images were acquired using a segmented-echo planar imaging (EPI) sequence to estimate FA and receive sensitivity maps. These low-resolution images were interpolated and co-registered with the high-resolution image (1×1×1 mm$^3$) acquired with the 3D FLASH sequence. The registrations were performed by a slightly modified version of a non-rigid registration algorithm. The actual FA corresponding to a nominal FA of 60° was determined by the two images acquired with the segmented gradient EPI sequence using FAs of 60° and 120°, respectively, and then the actual FA corresponding to a nominal FA of 17° was determined by the linear relationship between the real and nominal FAs with the measured FA from a nominal FA of 60°. The in vivo FA map of the body coil was shown in FIG. 14a. A minimal contrast brain image was acquired at TR/TE of 2000/16 ms with FA of 90° to estimate receive sensitivity. The calculated receive sensitivity of the 32 channel head coil was shown in FIG. 14b. CVs are 10.2% and 54.5% for the FA and the receive sensitivity maps, respectively. The variation of the actual FAs across a human brain was less than 3.0°. This small FA variation only led to slight contrast changes when FA was 17° (FIG. 14). In other words, the contrast was insensitive to the inhomogeneity of the transmit field. However, CNR inhomogeneity of the receive sensitivity still exists, which can be corrected as described below. For example, CNR inhomogeneity caused by non-uniform receive sensitivity can be corrected by measured receive sensitivity using Eq. 11

Figure 15:
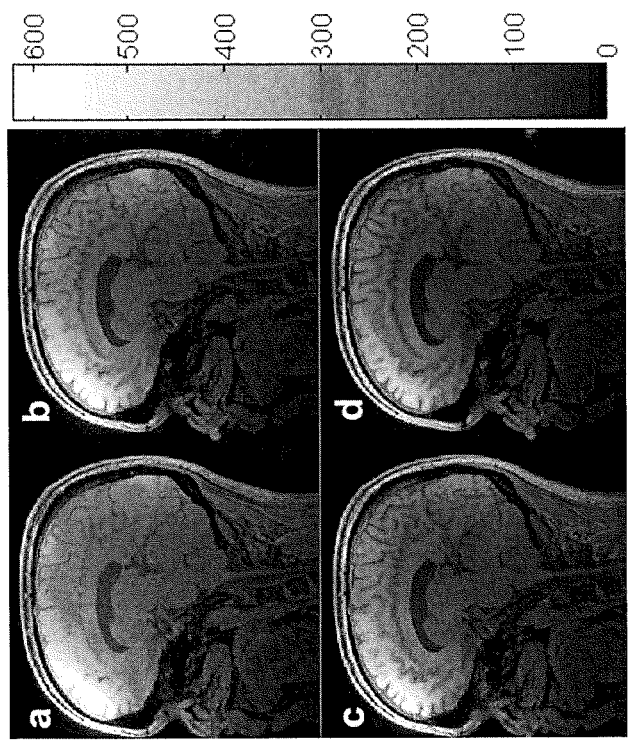
FIG. 15 illustrates in vivo brain images acquired using 3D FLASH sequence with the different flip angles of 9 degrees (a), 13 degrees (b), 17 degrees (c) and 20 degrees (d) and a TR of 13 ms.

FIG. 15 shows in vivo brain images acquired using the 3D FLASH sequence at TR of 13 ms with four different FAs: 9° (a), 13° (b), 17° (c), and 20° (d). When FA was 9°, which corresponds to the Ernst angle of the averaged GM and WM at TR=13 ms, signal intensity reached the maximum of 160 and GM-WM contrast was 7 (FIG. 15a). With increasing FA, signal intensity of brain tissues decreased but the contrast increased. At the FA of 17°, signal intensity reduced to 107 and the contrast was 20 (FIG. 15c). At the FA of 20°, signal intensity reduced to around 100 and the contrast decreased to 18 (FIG. 15d). The results from the in vivo experiment in FIG. 14 were consistent with the simulation results in FIG. 12, confirming the simulation method. Moreover, standard deviation of noise as a function of FA was determined by using the subtraction of two images acquired with identical imaging parameters but different time frames. The result showed that the standard deviation of noise was almost unchangeable when FA increased from 9 to 20°. Thus, the in vivo experiment confirmed that the optimized FA for maximum contrast efficiency should be around 17° at TR=13, consistent with the simulation results in FIGS. 12 and 13.

Figure 16:
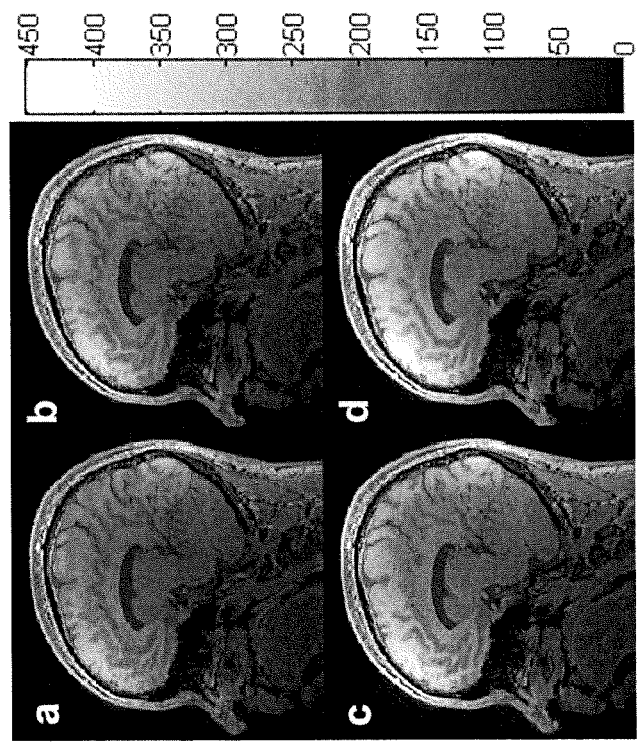
FIG. 16 illustrates in vivo brain images acquired using 3D FLASH sequence with the different TRs: TR=13 ms (a), 15 ms (b), 17 ms (c) and 19 ms (d) and the flip angle of 17°.

FIG. 16 shows in vivo brain images acquired using the 3D FLASH sequence at FA of 17° with four different TRs: 13 (a), 15 (b), 17 (c) and 19 (d) ms. When TR increased from 13 to 19 ms, total scan time increased from 235 to 393 seconds, and signal intensity of brain tissues increases about 50% and GM-WM contrast increased about 45%. The contrast efficiency slightly reduced with increasing TR, and was consistent with the simulation results in FIG. 12.

In order to correct the CNR inhomogeneity caused by receive sensitivity, a set of signal intensity images and/or phase images can be acquired using the optimal imaging parameters (e.g., parameters for reducing the sensitivity of the contrast inhomogeneity caused by the non-uniform acquisition conditions (described above). A receive sensitivity (or receive coil sensitivity map, receive coil profile, etc.) can be estimated by any known technique. For example, the receive sensitivity can be estimated from the set of signal intensity images and/or phase images or from electromagnetic field measurement. Then, the receive sensitivity (e.g., an image) can be registered with the set of signal intensity images to produce a relative correction matrix. For example, the receive sensitivity can be registered with the low resolution image acquired at the optimal FA to produce relative correction matrix. The relative correction matrix can be normalized to obtain a correction matrix. The relative correction matrix can be normalized to a predetermined value, for example, a value that keeps SNR or CNR constant before or after the correction. Finally, the influence of non-uniform receive sensitivity on the CNR inhomogeneity can be corrected by calculating a ratio of the set of signal intensity images and the correction matrix.

Figure 17:
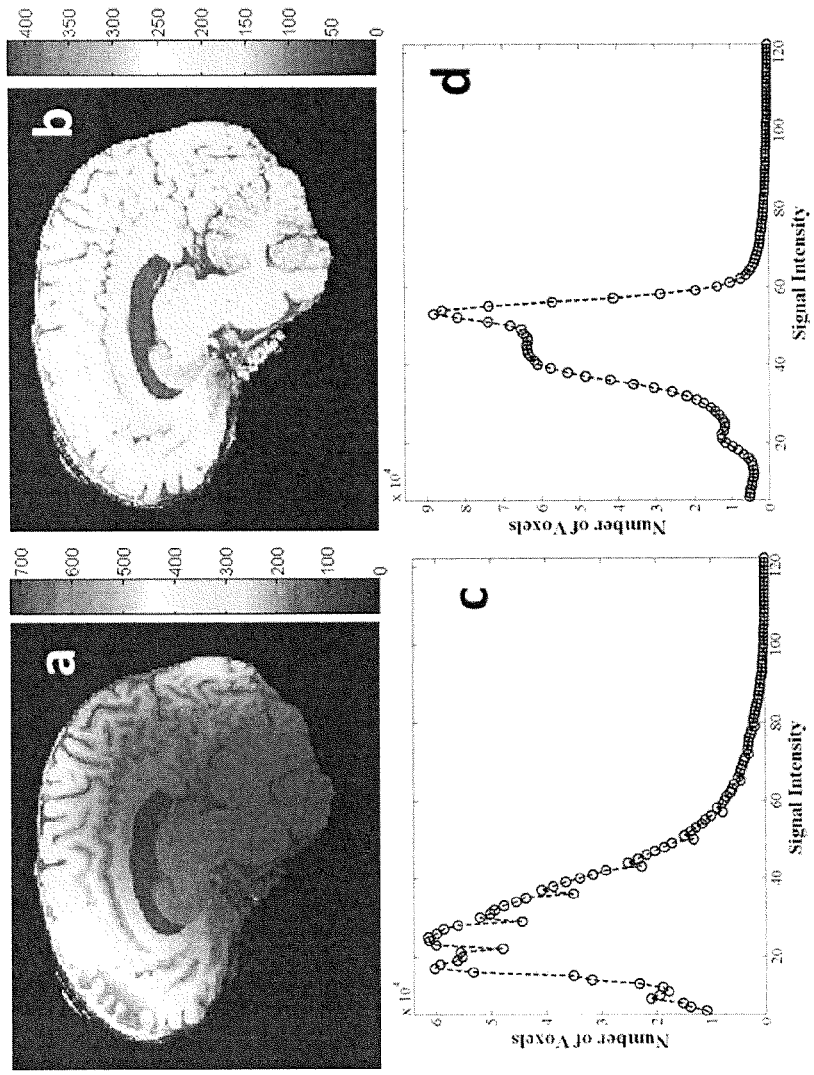
FIG. 17 illustrates in vivo brain image acquired using 3D FLASH sequence with optimal imaging parameters for tissue contrasts (a), the corrected image of CNR inhomogeneity (b) using measured receive sensitivity and their corresponding intensity histograms (c-d).

FIG. 17a shows that raw brain image acquired with FA=17° and TR=13° which is optimal imaging parameters for maximizing contrast efficiency of brain tissue. It is possible to visually distinguish GM and WM, in FIG. 17a. The intensity histogram of the raw in FIG. 16c was also flat and wide. In the raw image, there exist an apparent image inhomogeneity which also led to much higher signal intensity of both GM and WM in anterior and posterior regions of the brain, compared to other regions. Although the optimal FA of 17° was used to correct the influence of transmit field on contrast inhomogeneity, inhomogeneous receive sensitivity still impacted on the contrast inhomogeneity. Measured receive sensitivity can be used to correct the contrast inhomogeneity, shown in FIG. 17b. That is, CNR inhomogeneity can be corrected completely using optimal FA and measured receive sensitivity. After the CNR inhomogeneity correction, brain tissue became more uniform across a whole brain. The intensity histogram of the corrected image was show in FIG. 17d. The histogram was better separated, and the GM-WM peak was distinct. However, it is still observed visually signal inhomogeneity across a whole brain. For example, WM signal intensity at the top of brain (frontal lobe) was less than that in the bottom of brain (cerebellum). To quantify the quality of the images from the various correction methods, binary GM and WM masks were first obtained using the SPM segmentation algorithm, and then isolated GM and WM regions by multiplying the binary masks with the corrected images. CVs of the isolate WM and GM across the whole brain were computed. The CVs of GM and WM reduced from 10.7 and 8.2 before to 7.0 and 5.3 after the contrast inhomogeneity correction, respectively. Thus, these results demonstrated that the proposed method greatly reduced the variation of the contrast inhomogeneity for single brain tissues.

In summary, according to the simulation results and measured FA maps, the optimal FA can be chosen to not only maximize CNR efficiency but also reduce or remove the effect of transmit field on CNR inhomogeneity. In this case, CNR inhomogeneity only resulted from non-uniform receive sensitivity, and was corrected using Eq. 11 with measured receive sensitivity based on the minimum contrast method. Therefore, the proposed method can correct CNR inhomogeneity caused by both transmit field and receive sensitivity. The results in FIG. 16 showed that this method greatly improved tissue histograms.

It should be appreciated that the logical operations described herein with respect to the various figures may be implemented (1) as a sequence of computer implemented acts or program modules (i.e., software) running on a computing device, (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 18A:
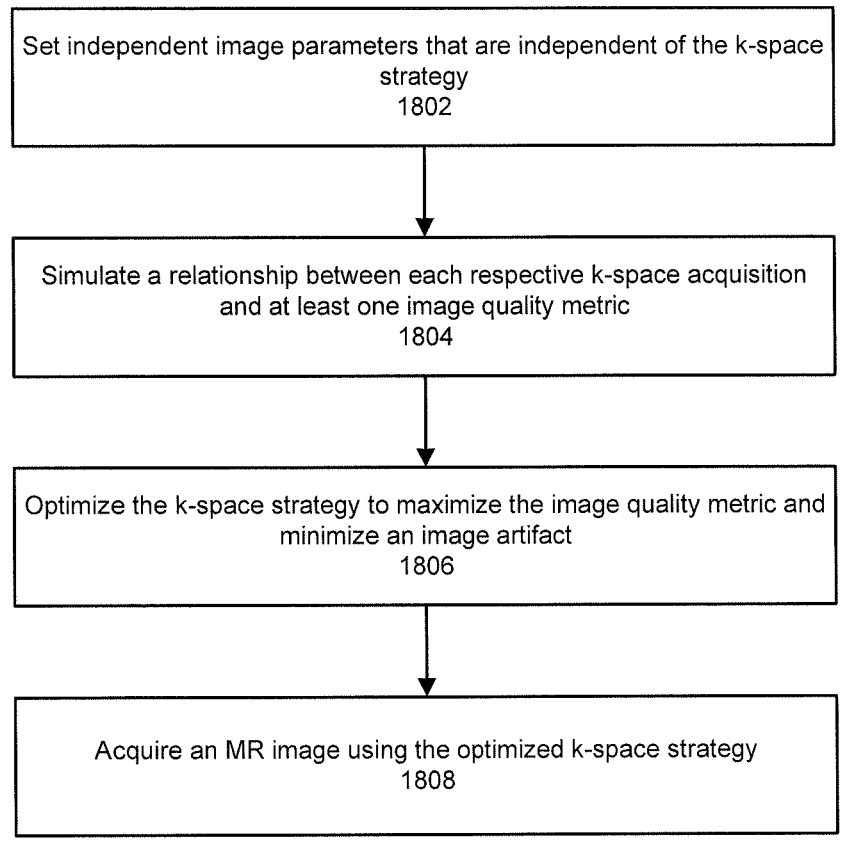
FIG. 18(a) is a flow diagram that illustrates example operations for optimizing k-space strategies.

Referring now to FIG. 18a, example operations for optimizing k-space strategies are shown. At 1802, independent image parameters are set, where the independent image parameters are independent of a k-space strategy in an imaging sequence. At 1804, a relationship between each respective k-space acquisition and at least one image quality metric is simulated. For example, the relationships can be simulated using Bloch equations (e.g., Eqs. 2 and 4 for MP-RAGE sequence and Eqs. 9 and 10 for FLASH sequence). Additionally, the image quality metric includes a contrast metric. At 1806, the k-space strategy is optimized to maximize the image quality metric and minimize an image artifact. Then, at 1808, an MR image is acquired using the optimized k-space strategy.

Figure 18B:
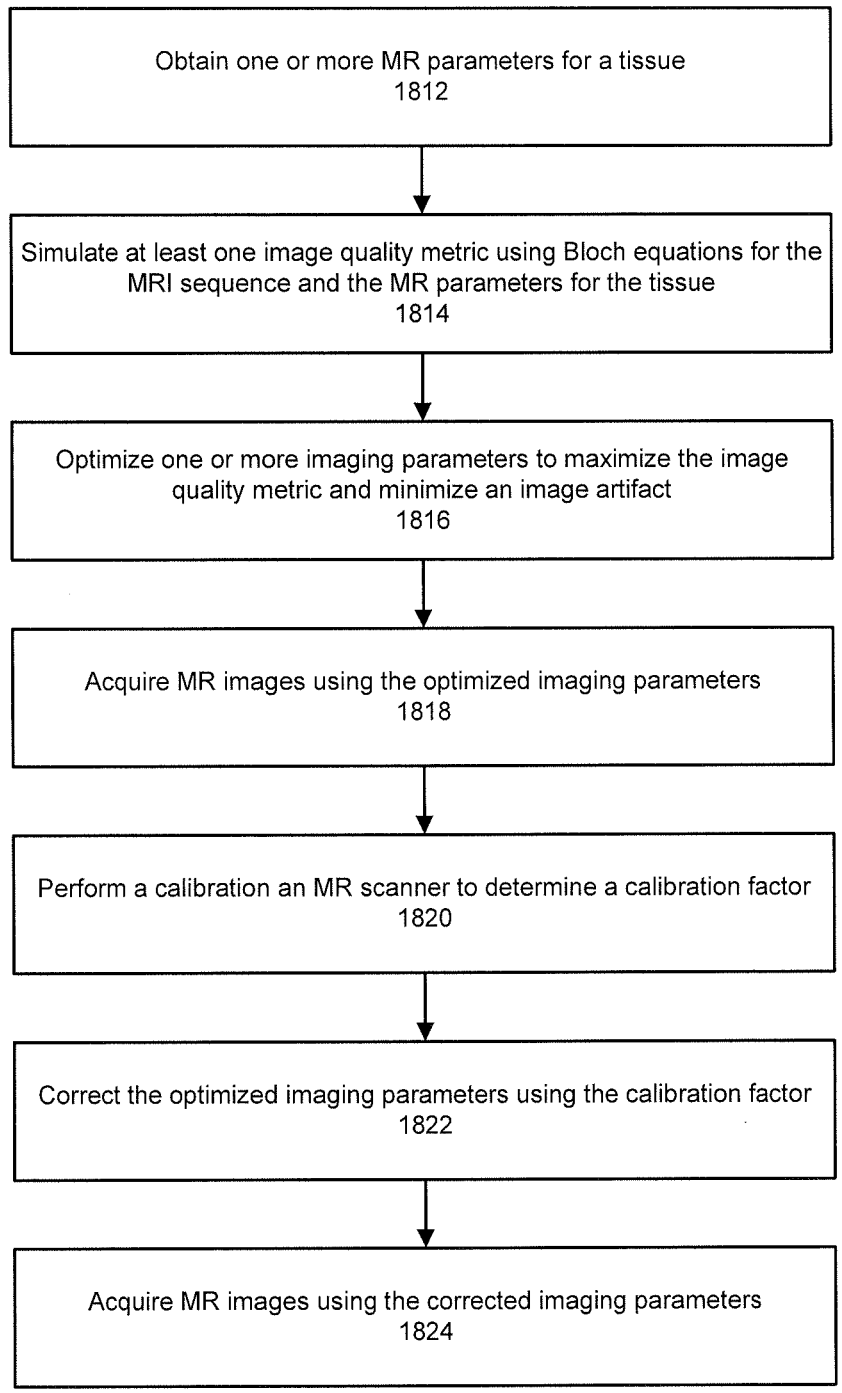
FIG. 18(b) is a flow diagram that illustrates example operations for optimizing imaging parameters.

Referring now to FIG. 18b, example operations for optimizing imaging parameters are shown. At 1812, one or more MR parameters for a tissue are obtained, where the tissue includes a normal or pathological (e.g., diseased) tissue. At 1814, at least one image quality metric using Bloch equations for the MRI sequence and the MR parameters for the tissue are simulated. For example, the image quality metric can be simulated using Bloch equations (e.g., Eqs. 2 and 4 for MP-RAGE sequences and Eqs. 9 and 10 for FLASH sequences). Additionally, the image quality metric includes a contrast metric. At 1816, one or more imaging parameters are optimized by maximizing the image quality metric and minimizing an image artifact. The, at 1818, the MRI images are acquired using the optimized imaging parameters. Optionally, at 1820, a calibration is performed on an MR scanner to determine a calibration factor, where the calibration factor relates theoretical imaging parameters to actual imaging parameters of the MRI scanner. Then, at 1822, the optimized imaging parameters are corrected based on the calibration factor. At 1824, the MR images are acquired with the MRI scanner using the corrected imaging parameters.

Figure 18C:
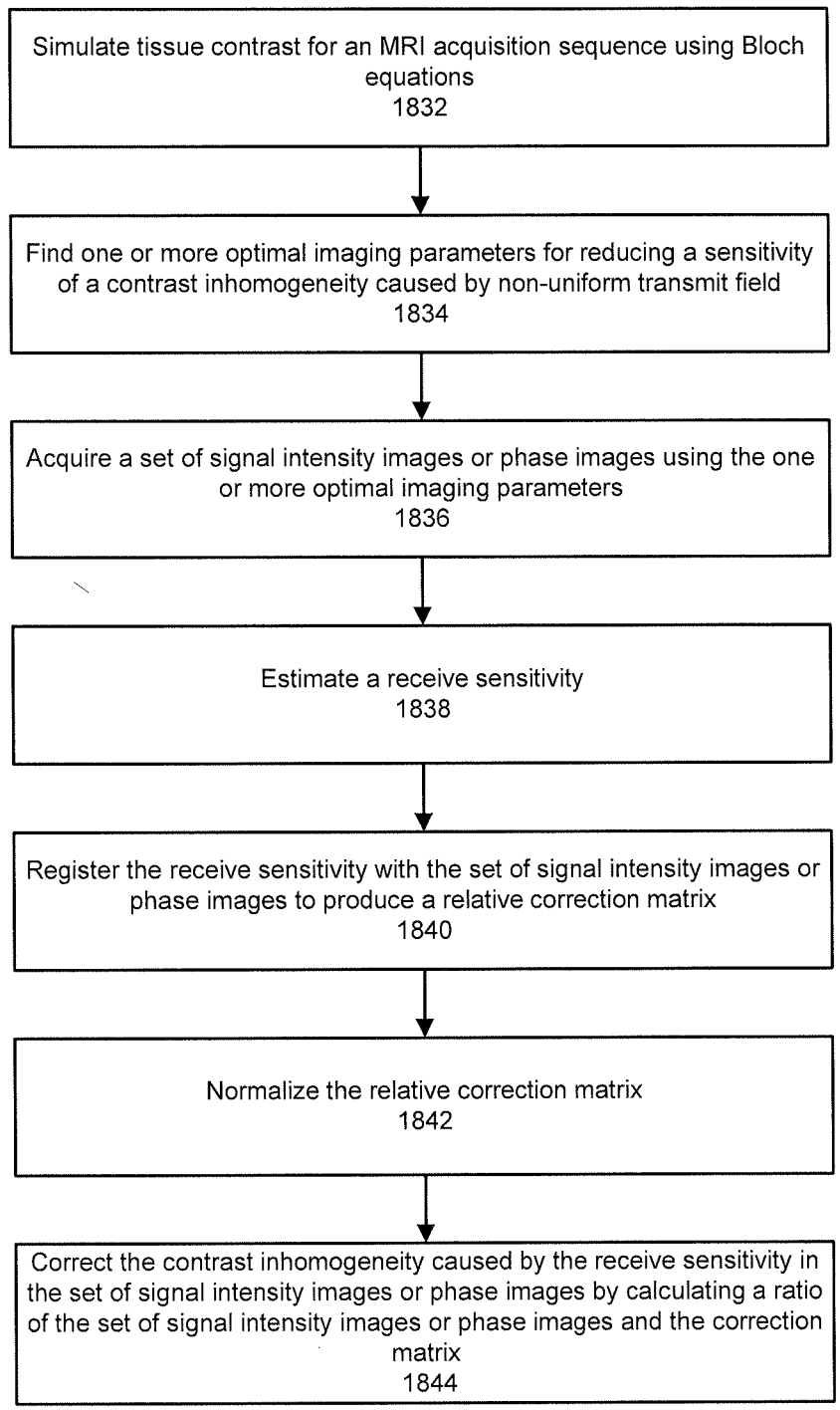
FIG. 18(c) is a flow diagram that illustrates example operations for correcting inhomogeneous contrast in an MRI image.

Referring now to FIG. 18c, example operations for correcting for inhomogeneous contrast in an MRI image are shown. At 1832, tissue contrast for an MRI acquisition sequence are simulated using Bloch equations. For example, the tissue contrast can be simulated using Bloch equations (e.g., Eqs. 2 and 4 for MP-RAGE sequences and Eqs. 9 and 10 for FLASH sequences). At 1834, one or more optimal imaging parameters for reducing a sensitivity of a contrast inhomogeneity caused by non-uniform acquisition conditions (e.g., non-uniform transmit field) can be found. At 1836, a set of signal intensity images and/or phase images is acquired using the one or more optimal imaging parameters. At 1838, a receive coil sensitivity map (or receive sensitivity, receive coil profile, etc.) is estimated, and at 1840, the receive sensitivity is registered with the set of signal intensity images and/or phase images to produce a relative correction matrix. Then, at 1842, the relative correction matrix is normalized to obtain a correction matrix. At 1844, the contrast inhomogeneity caused by the receive sensitivity in the set of signal intensity images is corrected by calculating a ratio of the set of signal intensity images and/or phase images and the correction matrix.

Figure 19:
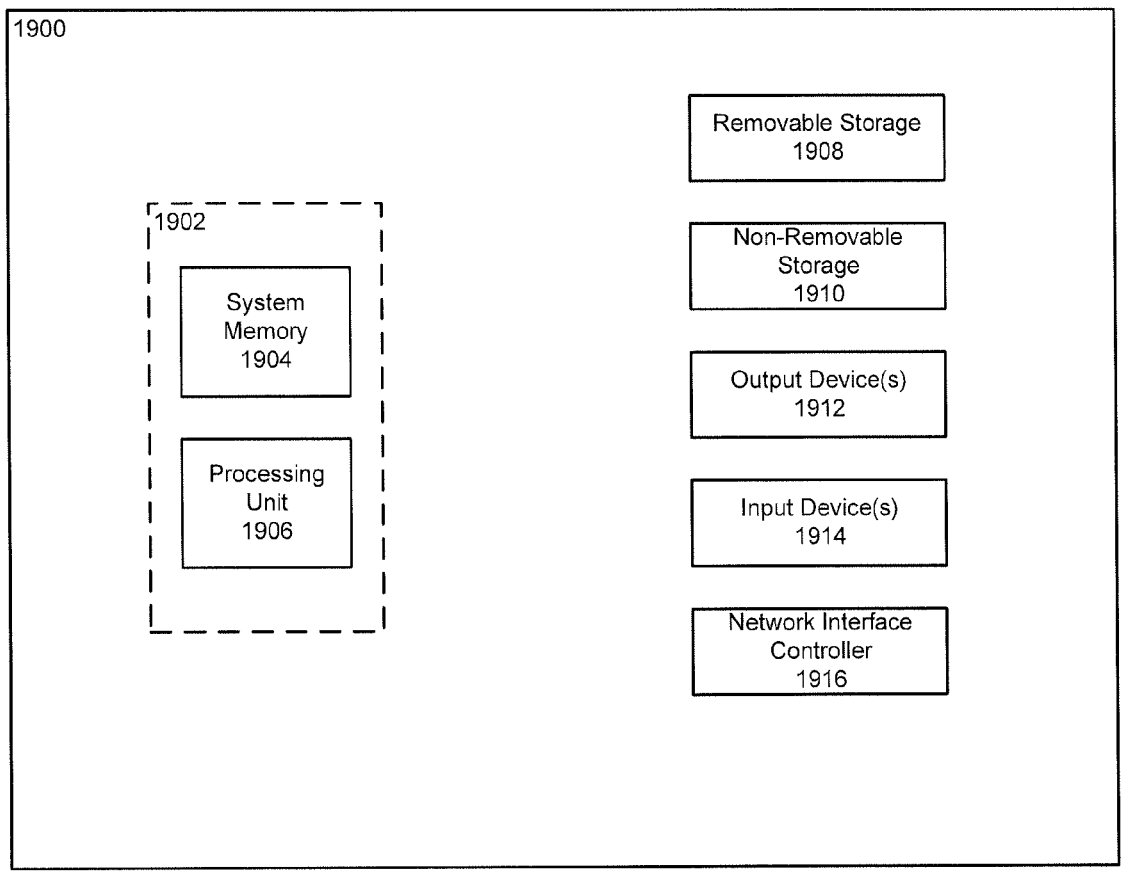
FIG. 19 is a block diagram that illustrates an example computing device.

When the logical operations described herein are implemented in software, the process may execute on any type of computing architecture or platform. For example, referring to FIG. 19, an example computing device upon which embodiments of the invention may be implemented is illustrated. In particular, the network device discussed above may be a computing device, such as computing device 1900 shown in FIG. 19. It should be understood that the computing device 1900 can be incorporated in or remote from an MRI scanner such as the example MRI scanner described above. The computing device 1900 may include a bus or other communication mechanism for communicating information among various components of the computing device 1900. In its most basic configuration, computing device 1900 typically includes at least one processing unit 1906 and system memory 1904. Depending on the exact configuration and type of computing device, system memory 1904 may be volatile (such as random access memory (RAM)), non-volatile (such as read-only memory (ROM), flash memory, etc.), or some combination of the two. This most basic configuration is illustrated in FIG. 19 by dashed line 1902. The processing unit 1906 may be a standard programmable processor that performs arithmetic and logic operations necessary for operation of the computing device 1900.

Computing device 1900 may have additional features/functionality. For example, computing device 1900 may include additional storage such as removable storage 1908 and non-removable storage 1910 including, but not limited to, magnetic or optical disks or tapes. Computing device 1900 may also contain network connection(s) 1916 that allow the device to communicate with other devices. Computing device 1900 may also have input device(s) 1914 such as a keyboard, mouse, touch screen, etc. Output device(s) 1912 such as a display, speakers, printer, etc. may also be included. The additional devices may be connected to the bus in order to facilitate communication of data among the components of the computing device 1900. All these devices are well known in the art and need not be discussed at length here.

The processing unit 1906 may be configured to execute program code encoded in tangible, computer-readable media. Computer-readable media refers to any media that is capable of providing data that causes the computing device 1900 (i.e., a machine) to operate in a particular fashion. Various computer-readable media may be utilized to provide instructions to the processing unit 1906 for execution. Common forms of computer-readable media include, for example, magnetic media, optical media, physical media, memory chips or cartridges, a carrier wave, or any other medium from which a computer can read. Example computer-readable media may include, but is not limited to, volatile media, non-volatile media and transmission media. Volatile and non-volatile media may be implemented in any method or technology for storage of information such as computer readable instructions, data structures, program modules or other data and common forms are discussed in detail below. Transmission media may include coaxial cables, copper wires and/or fiber optic cables, as well as acoustic or light waves, such as those generated during radio-wave and infra-red data communication. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 1906 may execute program code stored in the system memory 1904. For example, the bus may carry data to the system memory 1904, from which the processing unit 1906 receives and executes instructions. The data received by the system memory 1904 may optionally be stored on the removable storage 1908 or the non-removable storage 1910 before or after execution by the processing unit 1906.

Computing device 1900 typically includes a variety of computer-readable media. Computer-readable media can be any available media that can be accessed by device 1900 and includes both volatile and non-volatile media, removable and non-removable media. Computer storage media include volatile and non-volatile, and removable and non-removable media implemented in any method or technology for storage of information such as computer readable instructions, data structures, program modules or other data. System memory 1904, removable storage 1908, and non-removable storage 1910 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 1900. Any such computer storage media may be part of computing device 1900.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A method for optimizing k-space strategies for MR acquisition, comprising:
    setting independent image parameters, wherein the independent image parameters are independent of a k-space strategy in an imaging sequence;
    simulating, using a computing device, at least one respective image quality metric for each of a plurality of k-space acquisitions, wherein the image quality metric comprises a contrast metric;
    optimizing the k-space strategy, wherein optimizing the k-space strategy comprises using the simulated image quality metrics for each of the k-space acquisitions to select a sampling order in k-space center that maximizes the contrast metric and minimizes an image artifact caused by the k-space strategy; and
    acquiring at least one MR image using the optimized k-space strategy, wherein selecting a sampling order in k-space center further comprises:
    filling a k-space zero line using a k-space acquisition having a maximum contrast metric, wherein the contrast metric comprises at least one of a contrast, contrast efficiency, CNR or CNR efficiency, and
    designing the sampling order to minimize the image artifact caused by the k-space strategy, wherein the image artifact caused by the k-space strategy comprises at least one of signal inhomogeneity, SNR inhomogeneity, contrast inhomogeneity, CNR inhomogeneity, signal loss, geometry distortion or image ghost.

2. The method of claim 1, wherein optimizing the k-space strategy further comprises selecting a sampling order for a predetermined k-space trajectory.

3. The method of claim 2, wherein the k-space trajectory comprises at least one of a rectilinear, radial, echo planar imaging, spiral, projection reconstruction, random k-space, under-sampled k-space, or partial k-space sampling trajectory, and the sampling order comprise at least one of a sequential, centric, interleave, reverse, or random sampling order.

4. The method of claim 1, wherein simulating, using a computing device, at least one respective image quality metric for each of a plurality of k-space acquisitions further comprises using Bloch equations for the imaging sequence and MR parameters of a tissue.

5. The method of claim 1, wherein the imaging sequence comprises at least one of a gradient echo sequence, echo planar sequence, spin echo sequence, or combinations thereof with or without magnetization preparation.

6. The method of claim 1, wherein the image quality metric further comprises at least one of signal intensity, SNR or SNR efficiency, and the contrast metric comprises at least one of a contrast, contrast efficiency, CNR or CNR efficiency.

7. The method of claim 1, wherein optimizing the k-space strategy further comprises optimizing the k-space strategy under limited conditions, wherein the limited conditions comprise at least one of a predetermined k-space trajectory, predetermined sampling order or predetermined imaging parameters.

8. The method of claim 2, wherein optimizing the k-space strategy further comprises selecting the k-space trajectory and the sampling order that achieve a maximum contrast metric and a minimum image artifact.

* * * * *